(12) United States Patent
Lele et al.

(10) Patent No.: US 8,546,148 B2
(45) Date of Patent: Oct. 1, 2013

(54) COMPOSITION FOR USE AS AN ASSAY REAGENT

(75) Inventors: Bhalchandra Lele, Newark, DE (US); Pratap Singh, Wilmington, DE (US); Raphael Bartz, Newark, DE (US); Jason A. Kellogg, Bear, DE (US)

(73) Assignee: Siemens Healthcare Diagnostics Inc, Tarrytown, NY (US)

( * ) Notice: Subject to any disclaimer, the term of this patent is extended or adjusted under 35 U.S.C. 154(b) by 0 days.

(21) Appl. No.: 13/442,503

(22) Filed: Apr. 9, 2012

(65) Prior Publication Data

US 2012/0208297 A1 Aug. 16, 2012

Related U.S. Application Data

(62) Division of application No. 12/815,007, filed on Jun. 14, 2010, now abandoned.

(51) Int. Cl.
*G01N 21/76* (2006.01)
*G01N 33/53* (2006.01)
*C08F 226/06* (2006.01)
*C08F 226/10* (2006.01)
*C08F 220/58* (2006.01)

(52) U.S. Cl.
USPC ........... 436/501; 436/518; 436/534; 526/304; 526/263; 528/363; 528/361

(58) Field of Classification Search
None
See application file for complete search history.

(56) References Cited

U.S. PATENT DOCUMENTS

| | | |
|---|---|---|
| 4,945,146 A | 7/1990 | Kapmeyer et al. |
| 4,962,046 A | 10/1990 | Kapmeyer et al. |
| 5,232,981 A | 8/1993 | Kapmeyer et al. |
| 5,290,678 A | 3/1994 | Jackowski |
| 5,583,200 A | 12/1996 | Larue et al. |
| 5,710,008 A | 1/1998 | Jackowski |
| 5,744,358 A | 4/1998 | Jackowski |
| 5,756,682 A | 5/1998 | Wicks et al. |
| 5,795,725 A | 8/1998 | Buechler et al. |
| 5,807,675 A | 9/1998 | Davalian et al. |
| 5,830,680 A | 11/1998 | Meyerhoff et al. |
| 5,834,210 A | 11/1998 | Liu et al. |
| 5,834,220 A | 11/1998 | Wicks et al. |
| 5,846,738 A | 12/1998 | Seidel |
| 5,925,533 A | 7/1999 | Doth et al. |
| 5,947,124 A | 9/1999 | Buechler et al. |
| 5,981,203 A | 11/1999 | Meyerhoff et al. |
| 6,060,278 A | 5/2000 | Liu et al. |
| 6,072,040 A | 6/2000 | Dave et al. |
| 6,077,676 A | 6/2000 | Shi et al. |
| 6,114,180 A | 9/2000 | Doth et al. |
| 6,156,521 A | 12/2000 | Buechler et al. |
| 6,165,981 A | 12/2000 | Flaa et al. |
| 6,171,870 B1 | 1/2001 | Freitag |
| 6,190,916 B1 | 2/2001 | Liu et al. |
| 6,214,629 B1 | 4/2001 | Freitag et al. |
| 6,222,619 B1 | 4/2001 | Herron et al. |
| 6,251,581 B1 | 6/2001 | Ullman et al. |
| 6,268,481 B1 | 7/2001 | Morjana |
| 6,406,667 B1 | 6/2002 | Singh et al. |
| 6,406,913 B1 | 6/2002 | Ullman et al. |
| 6,410,341 B1 | 6/2002 | Freitag et al. |
| 6,429,026 B1 | 8/2002 | Pettersson et al. |
| 6,461,828 B1 | 10/2002 | Stanton et al. |
| 6,482,648 B2 | 11/2002 | Doth et al. |
| 6,491,923 B1 | 12/2002 | Dave et al. |
| 6,514,734 B1 | 2/2003 | Clapper et al. |
| 6,579,687 B1 | 6/2003 | Buechler et al. |
| 6,670,196 B1 | 12/2003 | Buechler |
| 6,867,011 B1 | 3/2005 | Babin et al. |
| 6,881,536 B1 | 4/2005 | Shah et al. |
| 6,939,678 B1 | 9/2005 | Buechler et al. |
| 6,991,907 B1 | 1/2006 | Buechler et al. |
| 7,109,023 B2 | 9/2006 | Kang et al. |
| 7,202,042 B2 | 4/2007 | Buechler |
| 7,256,000 B2 | 8/2007 | Goertz et al. |
| RE39,816 E | 9/2007 | Stanton et al. |
| 7,285,418 B2 | 10/2007 | Katrukha |
| 7,348,157 B2 | 3/2008 | Eriksson et al. |
| 7,381,552 B2 | 6/2008 | Menzler et al. |
| 7,498,028 B2 | 3/2009 | Goertz et al. |
| 2008/0102481 A1 | 5/2008 | Mattingly et al. |
| 2008/0261242 A1 | 10/2008 | Goix et al. |
| 2008/0305512 A1 | 12/2008 | Mattingly et al. |
| 2009/0042228 A1 | 2/2009 | Hess et al. |
| 2009/0065368 A1 | 3/2009 | Davis et al. |
| 2009/0068181 A1 | 3/2009 | Lee et al. |
| 2009/0087918 A1 | 4/2009 | Hess et al. |
| 2009/0148860 A1 | 6/2009 | Van Eyk et al. |
| 2009/0233268 A1 | 9/2009 | Lin et al. |
| 2009/0233312 A1 | 9/2009 | Gibbons et al. |
| 2009/0234202 A1 | 9/2009 | Goix et al. |
| 2010/0062475 A1 | 3/2010 | Hamaguchi et al. |

*Primary Examiner* — Shafiqul Haq
*Assistant Examiner* — Galina Yakoleva
(74) *Attorney, Agent, or Firm* — Theodore Leitereg

(57) ABSTRACT

A composition for use as an assay reagent comprises a solid support comprising a member of a signal producing system and a coating of a synthetic copolymer. The synthetic copolymer comprises a first polymerized monomer comprising a pendant moiety comprising a reactive functionality or a derivative of a reactive functionality and a second polymerized monomer comprising a pendant moiety comprising at least 1 carbon atoms and at least 2 heteroatoms. In some embodiments the copolymer comprises a polyethylenic backbone comprising the pendant moiety comprising a reactive functionality or a derivative of a reactive functionality and the pendant moiety comprising at least 1 carbon atom and at least 2 heteroatoms.

13 Claims, 3 Drawing Sheets

Synthesis of MAMDMA

Figure 2

Feed ratios of hydrophilic monomers:MAMDMA and copolymer structures

| SB No. | Polymer | Structure |
|---|---|---|
| 1 | Poly(HPMA-co-MA-Actl) (1:1)<br><br>HPMA = N-2-hydroxypropylmethacrylamide<br>MA-Actl = Methacrylamidoacetaldehyde | 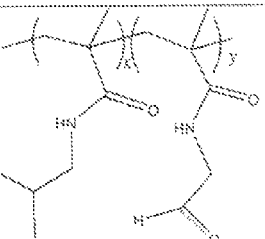 |
| 2 | Poly(HPMA-co-MA-Actl) (1:2) | Same as 1 except monomer ratios |
| 3 | Poly(HPMA-co-MA-Actl) (1:4) | Same as 1 except monomer ratios |
| 4 | Poly(Sulfobetaine-co-MA-Actl) (1:1)<br><br>Sulfobetaine=[2-methacryloyloxyethyl]- dimethyl (3-sulfopropyl)ammonium hydroxide | 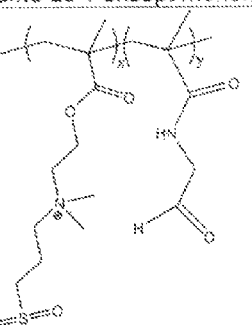 |
| 5 | Poly(MPEG$_{1100}$-MA-co-MA-Actl) (1:2)<br><br>MPEG$_{1100}$ = Methoxy-polyethyleneglycol$_{1100}$-methacrylate | 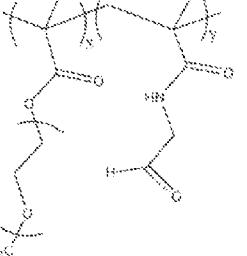 |
| 6 | Poly(AA-co-MA-Actl) (1:1)<br><br>AA = Acrylic acid | 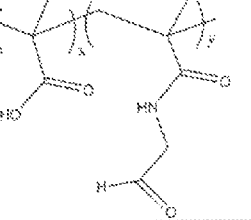 |

Figure 2 (cont'd):

Feed ratios of hydrophilic monomers:MAMDMA and copolymer structures

| SB No. | Polymer (Feed ratio) | Structure |
|---|---|---|
| 7 | Poly(MPEG$_{300}$-MA-co-MA-Actl) (1:1)<br><br>MPEG$_{300}$-MA = Methoxypolyethyleglycol$_{300}$ methacrylate | 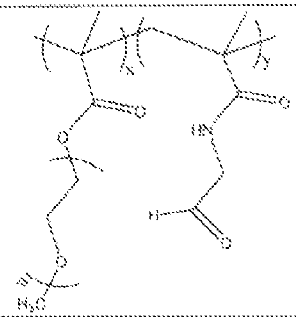 |
| 8 | Poly(NVP-co-MA-Actl) (1:1)<br><br>NVP = N-vinyl-2-pyrrolidone | 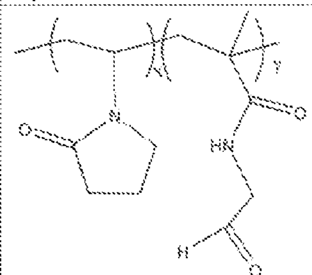 |

COMPOSITION FOR USE AS AN ASSAY REAGENT

This application is a Divisional of U.S. patent application Ser. No. 12/815,007 filed on Jun. 14, 2010, now abandoned, from which priority is claimed.

BACKGROUND

Dextran coating on particulate assay reagents has been employed to provide functional groups for conjugation to moieties such as biological moieties (e.g., antibodies). However, there is a significant variability in the chemical composition of dextran depending on the source.

There is a need for a coating having a reliable chemical composition to be used on the surface of particles for linking various moieties to the particles.

SUMMARY

One embodiment of the present invention is a composition that comprises a solid support comprising a member of a signal producing system (sps) and a coating of a synthetic copolymer. The synthetic copolymer comprises a first copolymerized monomer comprising a pendant moiety comprising a reactive functionality or a derivatized reactive functionality and a second copolymerized monomer comprising a pendant moiety comprising at least 1 carbon atom and at least 2 heteroatoms. In some embodiments the pendant moiety comprising a reactive functionality or a derivatized reactive functionality is a pendant moiety comprising an aldehyde or an aldehyde derivative.

Another embodiment of the present invention is a method of determining in a sample one or both of the presence and the amount of an analyte. The method comprises providing in combination in a medium the sample and the aforementioned composition, which also comprises a member of a specific binding pair (sbp) associated with the solid support, wherein the member of the specific binding pair binds to the analyte or to a second sbp member to form a complex related to the presence of the analyte. The combination is subjected to conditions for binding of the analyte to the composition to form a complex. The member of the signal producing system is activated and the amount of the complex is detected. The amount of the complex is related to one or both of the presence and the amount of analyte in the sample.

Another embodiment of the present invention is a method of determining in a sample one or both of the presence and the amount of an analyte. A combination is provided in a medium. The combination comprises the sample and a composition comprising a particle comprising an sps member, an sbp member that binds to the analyte or to a second sbp member to form a complex related to the presence of the analyte and a coating of a copolymer. The copolymer has the formula:

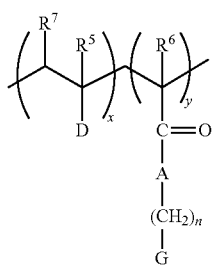

wherein:

D is (i) —COOR$^{10}$ wherein R$^{10}$ is H or alkyl of from 1 to 6 carbon atoms;

(ii)

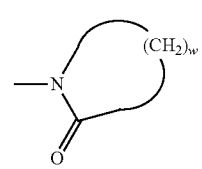

wherein:

w is 2-4; or (iii) —C(O)—X—(CH$_2$)$_p$—(Y)$_q$(CH$_2$)$_r$—Z wherein:

A is O or NR$^1$ wherein R$^1$ is H or alkyl of from 1 to 6 carbon atoms;

n is 1 to 10;

G is CHO; CH(OR$^8$)$_2$ wherein R$^8$ is alkyl of from 1 to 6 carbon atoms; COOH or a derivative thereof; NR$^1$ wherein R$^1$ is H or alkyl of from 1 to 6 carbon atoms and n is 1 to 10; OH; or a member of a specific binding pair;

X is O or NR$^2$ wherein R$^2$ is H or alkyl of from 1 to 6 carbon atoms;

Y is —(CH$_2$O)$_m$— wherein m is 1 to 1500; or N$^\oplus$(R$^3$R$^4$) wherein R$^3$ and R$^4$ are independently H or alkyl of from 1 to 6 carbon atoms;

p is 0 to 10, being at least 1 when Y is ⊕N$^\oplus$(R$^3$, R$^4$);

q is 0 or 1;

r is 0 to 10, being at least 1 when Y is ⊕N$^\oplus$(R$^3$, R$^4$); and

Z is SO$_3^-$; alkyl of from 1 to 6 carbon atoms; —(CHOH)$_t$(CH$_2$)$_u$CH$_3$ wherein t is 1 to 5 and u is 0 to 10;

R$^5$, R$^6$ and R$^7$ are independently H or alkyl of from 1 to 6 carbon atoms; and x and y are independently 1 to 1000.

The combination is subjected to conditions for binding of the sbp member to the analyte or to the second sbp member to form a complex. The sps member is activated and the amount of the complex is detected. The amount of the complex is related to one or both of the presence and the amount of analyte in the sample.

Another embodiment of the present invention is a copolymer of the formula:

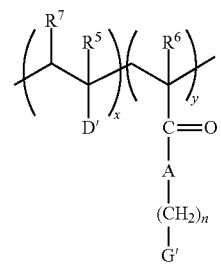

wherein:

A is O or NR¹ wherein R¹ is H or alkyl of from 1 to 6 carbon atoms;

n is 1 to 10;

G' is CHO; CH(OR⁸)₂ wherein R⁸ is alkyl of from 1 to 6 carbon atoms; a member of a specific binding pair;

D' is (i) —COOR¹⁰ wherein R¹⁰ is H or alkyl of from 1 to 6 carbon atoms;

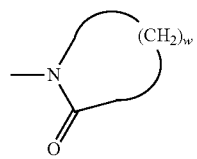

(ii)

wherein:

w is 2-4; or (iii) —C(O)—X—(CH₂)$_p$—(Y)$_q$—(CH₂)$_r$—Z' wherein:

X is O or NR² wherein R² is H or alkyl of from 1 to 6 carbon atoms;

Y is —(CH₂O)$_m$— wherein m is 1 to 1500, or ⊕N⊕(R³R⁴) wherein R³ and R⁴ are independently H or alkyl of from 1 to 6 carbon atoms;

p is 0 to 10, being at least 1 when Y is ⊕N⊕(R³, R⁴);

q is 0 or 1;

r is 0 to 10, being at least 1 when Y is ⊕N⊕(R³, R⁴); and

Z' is SO₃⁻; or alkyl of from 1 to 6 carbon atoms;

R⁵, R⁶ and R⁷ are independently H or alkyl of from 1 to 6 carbon atoms; and x and y are independently 1 to about 1000.

BRIEF DESCRIPTION OF DRAWINGS

FIG. 2 is a tabular depiction of structures of embodiments of copolymers in accordance with the present compositions after hydrolysis of an acetal protecting group. FIG. 2 also includes the feed ratios of hydrophilic monomers that were employed in the synthesis of the copolymers depicted.

DETAILED DESCRIPTION OF SPECIFIC EMBODIMENTS

Compositions

Figure 1:
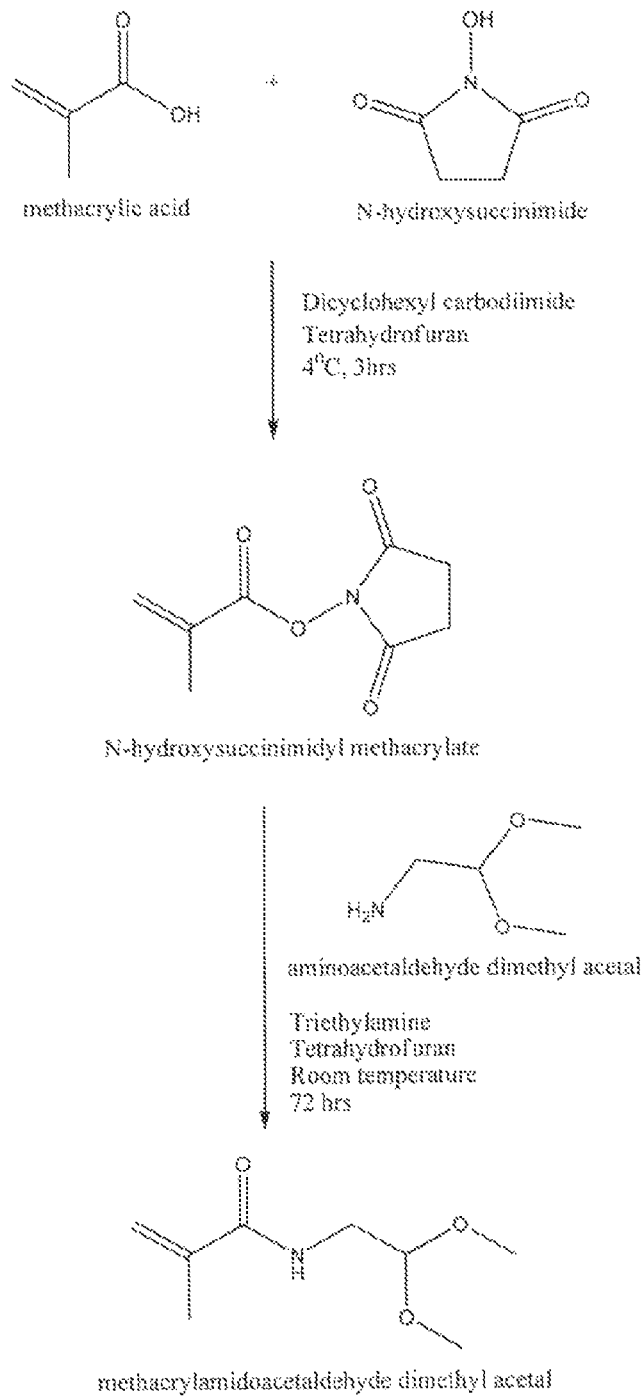
FIG. 1 is a schematic diagram of a synthesis of MAM-DMA.

In some embodiments a copolymer of the present compositions is a random copolymer where one of the monomer units of the copolymer comprises reactive functionalities for conjugation to molecules of interest such as, for example, particles and sbp members, and the other of the monomer units of the copolymer is functionalized to render the resulting copolymer hydrophilic. In some embodiments, the copolymer comprises two different monomer units, or three different monomer units, or four different monomer units, or five different monomer units, for example. In some embodiments, a first monomer unit comprises a reactive functionality or a derivative of a reactive functionality. A second monomer unit comprises a hydrophilic moiety. In some embodiments additional monomers (third, fourth and fifth monomers, for example) that comprise a reactive functionality or a derivative of a reactive functionality that is different from the reactive functionality or derivative of the reactive functionality of another of the monomers or that comprise a hydrophilic moiety that is different from the hydrophilic moiety of another monomer may be employed.

In a random copolymer the distribution of the copolymerized monomers may be such that at any point in the polymer chain a first copolymerized monomer and a second copolymerized monomer may alternate or may repeat as distinguished from block copolymers.

In some embodiments the number of each different copolymerized monomer in the copolymer is controlled during the preparation of the functionalized polymer by controlling the molar concentration of the monomer units that are employed in the preparation of the polymer. Thus, the number of each of the copolymerized monomers (x and y in the formulas below) is controlled in the final functionalized copolymer. The copolymer may be tailored, for example, to one or more of a particular support, to compositions comprising such supports and to the use of such composition.

The term "monomer" or "monomer unit" means a molecule capable of undergoing polymerization to form a polymer; the molecule comprises a polymerizable functionality. The number of monomer units depends on one or more of the number of atoms in the monomer unit chain and the composition of the monomer unit, for example.

As mentioned above, compositions for use in preparing assay reagents or for use as assay reagents comprise a solid support comprising an sps member and a coating of a synthetic copolymer. The synthetic copolymer comprises at least two monomers that are copolymerized to form the polymer. One of the copolymerized monomers comprises a polymer backbone and pendant moieties that comprise at least one reactive functionality or at least one derivative of a reactive functionality. The other of the copolymerized monomers comprises a hydrophilic moiety comprising at least 1 carbon atom and at least 2 heteroatoms. In some embodiments the copolymer comprises a polyethylenic backbone comprising the pendant moiety comprising a reactive functionality or a derivatized reactive functionality and the pendant moiety comprising at least 1 carbon atom and at least 2 heteroatoms, or at least 4 carbon atoms and at least 3 heteroatoms, or at least 4 carbon atoms and at least 2 heteroatoms, or at least 8 carbon atoms and at least 7 heteroatoms. The copolymerized monomers comprise a polymer backbone that comprises a chain of carbon atoms, from which one or more reactive functionality-containing moieties or derivative of a reactive functionality-containing moieties are pendant from the chain and one or more of the hydrophilic moieties are pendant from the chain of the copolymer backbone.

In some embodiments the other of the copolymerized monomers that comprises a hydrophilic moiety comprises from 1 to about 15 carbon atoms and from 1 to about 10 heteroatoms. The copolymerized monomers comprise a polymer backbone that comprises a chain of carbon atoms, from which one or more reactive functionality-containing moieties or derivative of a reactive functionality-containing moieties are pendant from the chain and one or more of the hydrophilic moieties are pendant from the chain of the copolymer backbone.

The number of carbon atoms in the chain of the backbone of the copolymer is dependent on the number and nature of each of the copolymerized monomer units such as, e.g., the number of carbon atoms in the polymerizable functionality of the monomer units, and the molecular weight of the copolymer, for example. The number of carbon atoms in the polymerizable functionality of the monomer unit may be 2 to about 20, or 2 to about 15, or 2 to about 10, or 2 to about 5, or 2 to about 4, or 2 to 3, or 3 to about 20, or 3 to about 15, or 3 to about 10, or 3 to about 5, or 3 to 4, for example. The number of carbon atoms in the monomer comprising a pendant reactive functionality-containing moiety or derivative of a reactive functionality-containing moiety (arbitrarily referred to herein as the first copolymerized monomer) is at least about 3, or at least about 4, or at least about 5, or at least about 6, or at least about 7, or at least about 8, or at least about 9, or at least about 10 and may be in the range of about 3 to about 15, or about 3 to about 10, or about 3 to about 9, or about 3 to about 8, or about 3 to about 7, or about 3 to about 6, or about 3 to about 5, or 3 to 4. The number of the first copolymerized monomer in the copolymer is dependent on one or more of the need for binding to an sbp member and the need for binding to the surface of a support. The number of the first copolymerized monomers in the copolymer is 1 to about 1,000, or 1 to about 750, or 1 to about 500, or 1 to about 250, or 1 to about 100, or 1 to about 50, or 2 to about 1,000, or 2 to about 750, or 2 to about 500, or 2 to about 250, or 2 to about 100, or 2 to about 50, or 5 to about 1,000, or 5 to about 750, or 5 to about 500, or 5 to about 250, or 5 to about 100, or 5 to about 50, or 10 to about 1,000, or to about 750, or 10 to about 500, or 10 to about 250, or 10 to about 100, or 10 to about 50, or 100 to about 1,000, or 100 to about 750, or 100 to about 500, or 100 to about 250, for example.

The term "polymerizable functionality" refers to a portion of a monomer unit that reacts with a portion of another molecule of the monomer or a portion of a molecule of a different monomer such as, for example, a moiety that comprises one or more double or triple bonds such as, for example, allyl groups, vinyl groups, acrylate groups, methacrylate groups, acrylamide groups and methacrylamide groups The term "reactive functionality" is a functionality that can react with a corresponding reactive functionality on another molecule to form a covalent bond. Such reactive functionalities include, by way of illustration and not limitation, aldehyde, carboxy, amino, imino, sulfhydryl and hydroxy, for example. In some embodiments the reactive functionality is an aldehyde and the first copolymerized monomer comprises an aldehyde moiety.

The term "derivative of a reactive functionality" means a moiety that is formed by the reaction of a reactive functionality with another moiety that comprises a functionality reactive with the reactive functionality thereby forming a covalent bond linking two molecules together to form the derivative. The derivative of a reactive functionality may comprise an acetal, a carboxy ester, an amide, an ether or a thioether, for example. In some embodiments the derivative of a reactive functionality may be a reaction product of a reactive functionality with a reactive functionality of a member of a specific binding pair (sbp member) whereby the sbp member becomes covalently bound to the copolymer. Functionalities on the sbp member may be present naturally on the sbp member or may be introduced synthetically into the sbp member. Such functionalities include, for example, amine groups, hydroxyl groups, sulfhydryl groups and carboxyl groups. In some embodiments the derivative of a reactive functionality may be a reaction product of a reactive functionality with a reactive functionality of a particle whereby the copolymer becomes covalently bound to the particle thereby providing a coating of the copolymer on the surface of the particle. Functionalities on the particle may be present naturally on the particle or may be introduced synthetically on the surface of the particle. Such functionalities include amine groups, hydroxyl groups, azide groups and carboxyl groups, for example. In some embodiments the derivative of a reactive functionality is an aldehyde derivative.

The term "aldehyde derivative" means a moiety that is formed by the reaction of an aldehyde group with another moiety that comprises a functionality reactive with an aldehyde group. The aldehyde derivative may be an acetal that results from the reaction of two alcohol functionalities with a carbonyl oxygen of an aldehyde. The aldehyde derivative may be a reaction product of an aldehyde group with a member of a specific binding pair (sbp member) by means of reaction of the aldehyde with a functionality of the sbp member. Functionalities on the sbp member may be present naturally on the sbp member or may be introduced synthetically into the sbp member. Such functionalities include, for example, amine groups. The reaction between an aldehyde group and an sbp member may be by means of, for example, Schiff's base formation between an alkyl amine or an aryl amine of the sbp member and the aldehyde group. The reaction may be by means of reductive amination involving the aldehyde group and an amine group of the sbp member. In other embodiments, the aldehyde derivatives include, for example, acetals and bisulphite addition compounds. In some embodiments the aldehyde functionality may react with a corresponding amine group on the surface of a particle whereby the particle becomes covalently bound to the copolymer thereby providing a coating of the copolymer on the surface of the particle. Functionalities on the particle may be present naturally on the particle or may be introduced synthetically on the surface of the particle.

The other of the copolymerized monomers (hydrophilic monomer or otherwise referred to herein arbitrarily as the second copolymerized monomer) of the copolymer comprises a polymerizable functionality that comprises at least 1 carbon atom and at least 2 heteroatoms, or at least 1 carbon atom and at least 3 heteroatoms, or at least 1 carbon atom and at least 4 carbon atoms, or at least 2 carbon atoms and at least 2 heteroatoms, or at least 2 carbon atoms and at least 3 heteroatoms, or at least 2 carbon atoms and at least 4 heteroatoms, or at least 3 carbon atoms and at least 3 heteroatoms, or at least 3 carbon atoms and at least 4 heteroatoms, or at least 4 carbon atoms and at least 3 heteroatoms, or at least 4 carbon atoms and at least 4 heteroatoms, for example. As mentioned above, the copolymerized monomers form a polymer backbone comprising a chain of carbon atoms, from which one or more pendant moieties depend from the chain. The number of carbon atoms in the polymerizable functionality of the second monomer unit may be 2 to about 20, or 2 to about 15, or 2 to about 10, or 2 to about 5, or 2 to about 4, or 2 to 3, or 3 to about 20, or 3 to about 15, or 3 to about 10, or 3 to about 5, or 3 to 4, for example.

In some embodiments the second copolymerized monomer of the copolymer comprises a polymerizable functionality and a pendant moiety that comprises from 1 to about 15 carbon atoms and from 1 to about 10 heteroatoms, or from 1 to about 10 carbon atoms and from 1 to about 10 heteroatoms, or from 1 to about 10 carbon atoms and from 1 to about 8 heteroatoms, or from 1 to about 10 carbon atoms and from 1 to about 6 heteroatoms, or from 1 to about 10 carbon atoms and from 1 to about 5 heteroatoms, or from 1 to about 8 carbon atoms and from 1 to about 8 heteroatoms, or from 1 to about 8 carbon atoms and from 1 to about 7 heteroatoms, or from 1 to about 8 carbon atoms and from 1 to about 7 heteroatoms, or from 1 to about 8 carbon atoms and from 1 to about 6 heteroatoms, or from 4 to about 8 carbon atoms and from 3 to about 7 heteroatoms, for example.

The number of carbon atoms of the pendant hydrophilic moiety is at least 1, or at least about 2, or at least about 3, or at least about 4, or at least about 5, or at least about 10, or at least about 20, or at least about 40, or at least about 60, or at least about 80, or at least about 100, or at least about 150, or at least about 200, or at least about 300, or at least about 400, and no more that about 2,500, or no more than about 2,000, or no more that about 1,500, or no more that about 1,100, for example. In some embodiments the number of carbon atoms of the pendant moiety is in the range of 1 to about 2,500, or 1 to about 2,000, or 1 to about 1,500, or 1 to about 1,200, or 1 to about 1,100, or 1 to about 1,000, or 1 to about 750, or 1 to about 500, or 1 to about 400, or 1 to about 300, or 1 to about 200, or 1 to about 100, or 1 to about 80, or 1 to about 60, or 1 to about 40, or 1 to about 20, or 1 to about 10, or 2 to about 2,500, or 2 to about 2,000, or 2 to about 1,500, or 2 to about 1,200, or 2 to about 1,100, or 2 to about 1,000, or 2 to about 750, or 2 to about 500, or 2 to about 400, or 2 to about 300, or 2 to about 200, or 2 to about 100, or 2 to about 80, or 2 to about 60, or 2 to about 40, or 2 to about 20, or 2 to about 10, or 3 to about 2,500, or 3 to about 2,000, or 3 to about 1,500, or 3 to about 1,200, or 3 to about 1,100, or 3 to about 1,000, or 3 to about 750, or 3 to about 500, or 3 to about 400, or 3 to about 300, or 3 to about 200, or 3 to about 100, or 3 to about 80, or 3 to about 60, or 3 to about 40, or 3 to about 20, or 3 to about 10, or 4 to about 2,500, or 4 to about 2,000, or 4 to about 1,500, or 4 to about 1,200, or 4 to about 1,100, or 4 to about 1,000, or 4 to about 750, or 4 to about 500, or 4 to about 400, or 4 to about 300, or 4 to about 200, or 4 to about 100, or 4 to about 80, or 4 to about 60, or 4 to about 40, or 4 to about 20, or 4 to about 10, or 5 to about 2,500, or 5 to about 2,000, or 5 to about 1,500, or 5 to about 1,200, or 5 to about 1,100, or 5 to about 1,000, or 5 to about 750, or 5 to about 500, or 5 to about 400, or 5 to about 300, or 5 to about 200, or 5 to about 100, or 5 to about 80, or 5 to about 60, or 5 to about 40, or 5 to about 20, or 5 to about 10, for example.

The number of molecules of the second copolymerized monomer in the copolymer is 1 to about 1,000, or 1 to about 750, or 1 to about 500, or 1 to about 250, or 1 to about 100, or 1 to about 50, or 2 to about 1,000, or 2 to about 750, or 2 to about 500, or 2 to about 250, or 2 to about 100, or 2 to about 50, or 5 to about 1,000, or 5 to about 750, or 5 to about 500, or 5 to about 250, or 5 to about 100, or 5 to about 50, or 10 to about 1,000, or to about 750, or 10 to about 500, or 10 to about 250, or 10 to about 100, or 10 to about 50, or 100 to about 1,000, or 100 to about 750, or 100 to about 500, or 100 to about 250, for example.

The number of heteroatoms of the pendant hydrophilic moiety of the second copolymerized monomer comprising at least 1 carbon atom and at least 2 heteroatoms is that which is sufficient to render the copolymer hydrophilic. The term "hydrophilic" refers to a property of a molecule that is polar and thus prefers neutral molecules or polar molecules and prefers polar solvents. Hydrophilic molecules have an affinity for other hydrophilic moieties compared to hydrophobic moieties. The number of heteroatoms is dependent on such factors as the number of carbon atoms in the pendant moiety, the nature of the support and the nature of an aldehyde derivative, if present, for example.

The number of heteroatoms of the pendant hydrophilic moiety is at least about 2, or at least about 3, or at least about 4, or at least about 5, or at least about 6, or at least about 7, or at least about, or at least about 8, or at least about 9, or at least about 10, or at least about 20, or at least about 30, or at least about 40, or at least about 50, or at least about 60, or at least about 70, or at least about 80, or at least about 90, or at least about 100, or at least about 150, and no more that about 1,500, or no more that about 1,200, or no more than about 1,100, or no more that about 1,000, for example. In some embodiments the number of heteroatoms is in the range of 2 to about 1,500, or 2 to about 1,250, or 2 to about 1,000, or 2 to about 750, or 2 to about 500, or about 2 to about 250, or 2 to about 100, or 2 to about 80, or 2 to about 60, or 2 to about 40, or 2 to about 20, or 2 to about 10, or 3 to about 1,500, or 3 to about 1,250, or 3 to about 1,000, or 3 to about 750, or 3 to about 500, or about 3 to about 250, or 3 to about 100, or 3 to about 80, or 3 to about 60, or 3 to about 40, or 3 to about 20, or 3 to about 10, or 5 to about 1,500, or 5 to about 1,250, or 5 to about 1,000, or 5 to about 750, or 5 to about 500, or 5 to about 250, or 5 to about 100, or 5 to about 80, or 5 to about 60, or 5 to about 40, or 5 to about 20, or 5 to about 10, or 7 to about 1,500, or 7 to about 1,250, or 7 to about 1,000, or 7 to about 750, or 7 to about 500, or about 7 to about 250, or 7 to about 100, or 7 to about 80, or 7 to about 60, or 7 to about 40, or 7 to about 20, or 7 to about 10, for example.

The hydrophilicity of the copolymer may be controlled by the number of heteroatoms (and functional groups comprising such heteroatoms) in the copolymer. The number of heteroatoms in the copolymer depends on the number of heteroatoms in each of the second copolymerized monomer and also on the number of copolymerized monomers comprising the heteroatoms compared with the number of copolymerized monomers that comprise a pendent moiety comprising a reactive functionality or a derivative of a reactive functionality. In some embodiments there is 1 heteroatom per about 3 carbon atoms, or 1 heteroatom per about 6 carbon atoms, or 1 heteroatom per about 10 carbon atoms, or 1 heteroatom per about 12 carbon atoms, or 1 heteroatom per about 15 carbon atoms, or 2 heteroatoms per 1 carbon atom, or 2 heteroatoms per about 2 carbon atoms, or 2 heteroatoms per about 3 carbon atoms, or 2 heteroatoms per about 4 carbon atoms, or 2 heteroatoms per about 6 carbon atoms, or 2 heteroatoms per about 10 carbon atoms, or 2 heteroatoms per about 12 carbon atoms, or 2 heteroatoms per about 15 carbon atoms, or 3 heteroatoms per about 4 carbon atoms, or 3 heteroatoms per about 6 carbon atoms, or 3 heteroatoms per about 10 carbon atoms, or 3 heteroatoms per about 12 carbon atoms, or 3 heteroatoms per about 15 carbon atoms, or 4 heteroatoms per about 4 carbon atoms, or 4 heteroatoms per about 6 carbon atoms, or 4 heteroatoms per about 10 carbon atoms, or 4 heteroatoms per about 12 carbon atoms, or 4 heteroatoms per about 15 carbon atoms, or 5 heteroatoms per about 4 carbon atoms, or 5 heteroatoms per about 6 carbon atoms, or 5 heteroatoms per about 10 carbon atoms, or 5 heteroatoms per about 12 carbon atoms, or 5 heteroatoms per about 15 carbon atoms, or 6 heteroatoms per about 5 carbon atoms, or 6 heteroatoms per about 6 carbon atoms, or 6 heteroatoms per about 10 carbon atoms, or 6 heteroatoms per about 12 carbon atoms, or 6 heteroatoms per about 15 carbon atoms, or 7 heteroatoms per about 7 carbon atoms, or 7 heteroatoms per about 8 carbon atoms, or 7 heteroatoms per about 10 carbon atoms, or 7 heteroatoms per about 12 carbon atoms, or 7 heteroatoms per about 15 carbon atoms, for example.

In some embodiments the pendant moiety of the second polymerized monomer (hydrophilic monomer) may comprise at least 1 carbon atom and at least 2 heteroatoms, or at least 1 carbon atom and at least 3 heteroatoms, or at least 1 carbon atom and at least 4 carbon atoms, or at least 2 carbon atoms and at least 2 heteroatoms, or at least 2 carbon atoms and at least 3 heteroatoms, or at least 2 carbon atoms and at least 4 heteroatoms, or at least 3 carbon atoms and at least 3 heteroatoms, or at least 3 carbon atoms and at least 4 heteroatoms, or at least 4 carbon atoms and at least 2 heteroatoms, or at least 4 carbon atoms and at least 3 heteroatoms, or at least 4 carbon atoms and at least 4 heteroatoms, or at least 4 carbon atoms and at least 5 heteroatoms, or at least 5 carbon atoms and at least 2 heteroatoms, or at least 5 carbon atoms and at least 3 heteroatoms, or at least 5 carbon atoms and at least 4 heteroatoms, or at least 5 carbon atoms and at least 5 heteroatoms, or at least 5 carbon atoms and at least 6 heteroatoms, or at least 6 carbon atoms and at least 2 heteroatoms, or at least 6 carbon atoms and at least 3 heteroatoms, or at least 6 carbon atoms and at least 4 heteroatoms, or at least 6 carbon atoms and at least 5 heteroatoms, or at least 6 carbon atoms and at least 6 heteroatoms, or at least 6 carbon atoms and at least 7 heteroatoms, or at least 7 carbon atoms and at least 2 heteroatoms, or at least 7 carbon atoms and at least 3 heteroatoms, or at least 7 carbon atoms and at least 4 heteroatoms, or at least 7 carbon atoms and at least 5 heteroatoms, or at least 7 carbon atoms and at least 6 heteroatoms, or at least 7 carbon atoms and at least 7 heteroatoms, or at least 7 carbon atoms and at least 8 heteroatoms, or at least 8 carbon atoms and at least 2 heteroatoms, or at least 8 carbon atoms and at least 3 heteroatoms, or at least 8 carbon atoms and at least 4 heteroatoms, or at least 8 carbon atoms and at least 5 heteroatoms, or at least 8 carbon atoms and at least 6 heteroatoms, or at least 8 carbon atoms and at least 7 heteroatoms, or at least 8 carbon atoms and at least 8 heteroatoms, or at least 8 carbon atoms and at least 9 heteroatoms, for example.

The number of copolymerized monomers comprising the heteroatoms compared with the number of polymerized monomers that comprise a pendent moiety comprising a reactive functionality or a derivative of a reactive functionality may be controlled by the feed ratio of the monomers during polymerization. Accordingly, during a polymerization the feed ratio of the monomer comprising the pendent moiety comprising a reactive functionality or a derivative of a reactive functionality (first copolymerizable monomer) may be increased over that of the hydrophilic monomer (second copolymerizable monomer). The ratio of the second copolymerizable monomer to the first copolymerizable monomer during a polymerization may be 1:1, or 1:1.5, or 1:2, or 1:2.5, or 1:3, or 1:3.5, or 1:4, or 1:4.5, or 1:5, or 1:5.5, or 1:6, for example. This feed ratio controls the value of x and y in the formulas below. In addition, the ratio of the second copolymerizable monomer to the first copolymerizable monomer can be adjusted to control the amount of signal obtained from a solid support comprising a member of a signal producing system (sps) and a coating of the synthetic copolymer. By having more of the first copolymerizable monomer comprising a pendant moiety comprising a reactive functionality, one can obtain a greater amount of derivatized reactive functionality on the solid support. In this manner, one can balance the hydrophilic properties of the resulting solid support with coated synthetic copolymer and the number of derivatized reactive functionalities to accommodate a wide variety of assays and signal producing systems.

The heteroatoms of the pendant hydrophilic moiety include, for example, oxygen, sulfur, nitrogen and phosphorus, and combinations of oxygen, sulfur, nitrogen and phosphorus. The heteroatoms may be present in combination with other one another or with other atoms such as, for example, one or more of hydrogen and carbon, in the form of one or more hydrophilic groups. In some embodiments, oxygen may be present as oxo or oxy bonded to one or more of hydrogen, carbon, sulfur, nitrogen and phosphorous; nitrogen may be bonded to one or more of hydrogen, carbon, oxygen, sulfur and phosphorus such as, for example, an azo, cyano, isocyano, nitro, nitroso, amido or amino group; sulfur is analogous to oxygen as discussed above; phosphorous may be bonded to one or more of hydrogen, carbon, sulfur, oxygen and nitrogen, such as, for example, a phosphonate or phosphate mono- or diester group.

The number of hydrophilic groups in the pendant hydrophilic moiety may be 2 to about 1,500, or 2 to about 1,250, or 2 to about 1,000, or 2 to about 750, or 2 to about 500, or 2 to about 250, or 2 to about 125, or 2 to about 100, or 2 to about 80, or 2 to about 60, or 2 to about 40, or 2 to about 20, or 2 to about 10, or 2 to about 5, or 3 to about 1,500, or 3 to about 1,250, or 3 to about 1,000, or 3 to about 750, or 3 to about 500, or 3 to about 250, or 3 to about 125, or 3 to about 100, or 3 to about 80, or 3 to about 60, or 3 to about 40, or 3 to about 20, or 3 to about 10, or 3 to about 5, or 4 to about 1,500, or 4 to about 1,250, or 4 to about 1,000, or 4 to about 750, or 4 to about 500, or 4 to about 250, or 4 to about 125, or 4 to about 100, or 4 to about 80, or 4 to about 60, or 4 to about 40, or 4 to about 20, or 4 to about 10, or 4 to 5; the hydrophilic groups may be independently one or more of the groups mentioned below.

In some embodiments, the hydrophilic group or groups of the pendant hydrophilic moiety, by way of illustration and not limitation, may be selected from an amine group (a primary, secondary, tertiary or quaternary amine), an amide group, a hydroxyl group, an ester group, an ether group, a polyether group (e.g., a polyoxyethylene group and a polyoxypropylene group), an epoxide group, a thioether group, a polythioether group, a sulfate group, a sulfite group, a phosphate group, a phosphite group, a phosphatidylcholine group, a betaine group, a sulfobetaine group, a nitrile group, an isonitrile group, a cyanate group, an isocyanate group, a thiocyanate group, an isothiocyanate group, an azide group, a thiol group, a thiolate group, a sulfide group, a sulfinate group, a sulfonate group, a phenolate group, a carbonyl group, a carboxylate group, a phosphine group, a phosphine oxide group, a phosphonic acid group and a phosphoramide group, as well as combinations and mixtures of such groups. In some embodiments, the hydrophilic group or groups, by way of illustration and not limitation, may be selected from the groups consisting of amine groups (primary, secondary, tertiary or quaternary amines), amide groups, hydroxyl groups, ester groups, ether groups, polyether groups, thioether groups, sulfate groups, sulfite groups, phosphate groups, phosphite groups, phosphatidylcholine groups, betaine groups and sulfobetaine groups.

In some embodiments the molecular weight (Daltons) (Da) of the copolymer is about 300 to about 10,000,000 or more, or about 500 to about 10,000,000, or about 1,000 to about 10,000,000, or about 10,000 to about 10,000,000, or about 100,000 to about 10,000,000, or 300 to about 5,000,000 or more, or about 500 to about 5,000,000, or about 1,000 to about 5,000,000, or about 10,000 to about 5,000,000, or about 100,000 to about 5,000,000, or 300 to about 1,000,000 or more, or about 500 to about 1,000,000, or about 1,000 to about 1,000,000, or about 10,000 to about 1,000,000, or about 100,000 to about 1,000,000, or about 100 to about 750,000, or about 500 to about 750,000, or about 1,000 to about 750,000, or about 10,000 to about 750,000, or about 100,000 to about 750,000, or about 100 to about 500,000, or about 200 to about 500,000, or about 1,000 to about 500,000, or about 10,000 to about 500,000, or about 100,000 to about 500,000, for example.

In some embodiments the copolymer comprises a polyethylenic backbone from which depend one or more reactive functionality-containing moieties or derivative of reactive functionality-containing such as, for example, one or more aldehyde-containing moieties or aldehyde derivative-containing moieties and one or more moieties comprising at least 1 carbon atom and at least 2 heteroatoms. The polyethylenic backbone comprises a linear chain of ethylenic groups, i.e., —(CHR—CHR)— groups (where R is alkyl or hydrogen) formed from monomers comprising double bonds. Other types of polymer backbones are also included and depend on the nature of the monomers. The monomers from which the copolymer is formed include, by way of example and not limitation, vinyl monomers, allylic monomers, olefins, and any small molecules containing at least one degree of unsaturation, and mixtures or two or more of the above monomers wherein the polymerizable functionality is a carbon-carbon double bond or a carbon-carbon triple bond. Besides the polymerizable functionality the monomer also comprises an appropriate substitution of either a reactive functionality or a derivative of a reactive functionality or at least 1 carbon atom and at least 2 heteroatoms. Classes of vinyl monomers include, but are not limited to, methacrylic acid, methacrylates, methacrylamide, N- and N,N-disubstituted methacrylamides, vinyl aromatic monomers, vinyl halides, vinyl esters of carboxylic acids (e.g., vinyl acetate), ethylene oxide acrylates, diacrylates, and dimethacrylates.

Examples of methacrylates include methacrylates appropriately substituted with a pendant moiety in accordance with present embodiments wherein the methacrylates include, by way of illustration and not limitation, methyl methacrylate, ethyl methacrylate, propyl methacrylate, isopropyl methacrylate, n-butyl methacrylate, iso-butyl methacrylate, and tert-butyl methacrylate, for example. Examples of vinyl aromatic monomers that may be used include, but are not limited to, appropriately substituted styrene, styrene-butadiene, p-chloromethylstyrene and divinyl benzene, for example. Vinyl halides that may be used include, but are not limited to, appropriately substituted vinyl chloride and vinylidene fluoride. Vinyl esters of carboxylic acids that may be used include, but are not limited to, appropriately substituted vinyl acetate, vinyl butyrate, vinyl 3,4-dimethoxybenzoate, vinyl malate and vinyl benzoate.

The copolymer is synthesized according to standard polymer chemistry for the synthesis of random copolymers using the appropriate monomeric units as identified above. In some embodiments, monomer units comprising one or more polymerizable functionalities may be combined in a single polymerization step. As mentioned above, in this latter polymerization approach, the number of each of the copolymerized monomers of the copolymer may be controlled by controlling the molar concentration of the monomer units.

The random copolymers may be prepared by any polymerization technique for the preparation of random copolymers. Polymerization techniques include, for example, radical polymerization, atom transfer radical polymerization, reversible addition fragmentation and chain transfer polymerization, nitroxide mediated polymerization, and so forth. The conditions for the polymerization such as, for example, temperature, reaction medium, pH, duration, and the order of addition of the reagents are dependent on one or more of the type of polymerization employed, the nature of the monomer reagents including any polymerizable functionality employed and the nature of any catalyst employed, for example. Such conditions are generally known since the types of polymerization techniques that can be used are well-known in the art.

As mentioned above, a composition in accordance with some of the present embodiments comprises a solid support comprising an sps member and a coating of the synthetic copolymer. The solid support may be comprised of an organic or inorganic, water insoluble material, which may be transparent or partially transparent. The solid support has a surface that is hydrophobic and can have any of a number of shapes such as, for example, particulate, including beads and particles, film, membrane, tube, well, strip, rod, and planar surfaces such as, e.g., plate. Depending on the type of assay, the solid support may or may not be suspendable in the medium in which it is employed. Examples of a suspendable solid support include polymeric materials such as latex particles and magnetic particles. Other solid support compositions include polymers, such as poly(vinyl chloride), polyacrylamide, polyacrylate, polyethylene, polypropylene, poly-(4-methylbutene), polystyrene, polymethacrylate, poly(ethylene terephthalate), nylon, and poly(vinyl butyrate), for example; either used by themselves or in conjunction with other materials.

In some embodiments the solid support is a particle. The particles generally have an average diameter of about 0.02 to about 100 microns, or about 0.05 to about 100 microns, or about 0.1 to about 100 microns, or about 0.5 to about 100 microns, or about 0.02 to about 50 microns, or about 0.05 to about 50 microns, or about 0.1 to about 50 microns, or about 0.5 to about 50 microns, or about 0.02 to about 20 microns, or about 0.05 to about 20 microns, or about 0.1 to about 20 microns, or about 0.5 to about 20 microns, for example. In some embodiments, the particles have an average diameter from about 0.05 microns to about 20 microns or from about 0.3 microns to about 10 microns, or about 0.3 microns to about 5 microns, for example. In some embodiments, the particles are latex particles or chrome particles.

A latex particle is a particulate water suspendable, water insoluble polymeric material. In some embodiments the latex is a substituted polyethylene such as polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyridine, vinyl-chloride acrylate copolymers, and the like.

Polymeric particles can be formed from addition or condensation polymers. The particles will be readily dispersible in an aqueous medium and can be functionalizable so as to permit conjugation to one or more of a copolymer as described herein, a member of a signal producing system (sps), and a member of a specific binding pair (sbp), for example. The particles can also be derived from naturally occurring materials, naturally occurring materials that are synthetically modified, and synthetic materials. In some embodiments the particles have, either naturally occurring or synthetically introduced, a reactive functionality such as, for example, amine groups, which are reactive with a corresponding reactive functionality of the copolymer such as, for example, aldehyde groups.

As mentioned above, the copolymer is a coating on the support. Coating the support with the copolymer may be accomplished in a number of ways. The copolymer may be attached to the surface of the support covalently. In some embodiments, covalent attachment may be accomplished by reaction of some of the reactive functionalities such as, for example, aldehyde groups, of the copolymer with a functionality on the surface of the support in a manner similar to that discussed above with regard to the aldehyde derivative. As mentioned above, in some embodiments, depending on the nature of the support, suitable functionalities may be already present on the surface of the support or they may be synthetically introduced on the surface. The remaining reactive functionalities such as, for example, aldehyde groups, are available for reaction with a suitably functionalized sbp member, for example.

In some embodiments, the amount of the copolymer coated on the support is dependent on one or more of the nature of the support, the nature of the copolymer, the nature of the sps member, whether attachment of the copolymer to the support is by virtue of the aldehyde bearing site, and whether an sbp member is attached to the aldehyde bearing site, for example.

In some embodiments the amount (percent by weight) of copolymer coated on the support is about 0.1 to about 10%, or about 0.1 to about 9%, or about 0.1 to about 8%, or about 0.1 to about 7%, or about 0.1 to about 6%, or about 0.1 to about 5%, or about 0.1 to about 4%, or about 0.1 to about 3%, or about 0.1 to about 2%, or about 0.1 to about 1%, or about 0.1 to about 0.5%, or about 1 to about 10%, or about 1 to about 9%, or about 1 to about 8%, or about 1 to about 7%, or about 1 to about 6%, or about 1 to about 5%, or about 1 to about 4%, or about 1 to about 3%, or about 1 to about 2%, or about 0.05 to about 0.5%, or about 0.06 to about 0.5%, or about 0.07 to about 0.5%, or about 0.08 to about 0.5%, or about 0.09 to about 0.5%, or about 0.1 to about 0.5%, or about 0.05 to about 0.4%, or about 0.06 to about 0.4%, or about 0.07 to about 0.4%, or about 0.08 to about 0.4%, or about 0.09 to about 0.4%, or about 0.1 to about 0.4%, or about 0.05 to about 0.3%, or about 0.06 to about 0.3%, or about 0.07 to about 0.3%, or about 0.08 to about 0.3%, or about 0.09 to about 0.3%, or about 0.1 to about 0.3%, or about 0.05 to about 0.2%, or about 0.06 to about 0.2%, or about 0.07 to about 0.2%, or about 0.08 to about 0.2%, or about 0.09 to about 0.2%, or about 0.1 to about 0.2%, for example.

The selection of a copolymer coating for a particle comprising a member of a signal producing system depends on one or more of a number of factors such as, for example, the type of assay, the nature of the member of the signal producing system, the expected concentration range of the analyte, the physical characteristics and origin of the antibody, the variation in effective antibody coating density, the pH of the final reaction mixture, and the ionic strength of the final reaction mixture. Depending on such factors, one copolymer coating may be preferred over another copolymer coating in any particular application. For example, the effective antibody coating density may be optimal for a signal producing system when a particular antibody is conjugated to a particular copolymer coating. The amount of signal may be controlled, for example, by adjusting the feed ratios of the first and second polymerizable monomers during copolymerization.

As mentioned above, the composition also comprises an sps member. The nature of the sps member depends on the type of assay in which embodiments of the present compositions may be employed. Such assays include, for example, immunoprecipitin and agglutination methods and corresponding light scattering techniques such as, e.g., nephelometry and turbidimetry, for the detection of antibody complexes; and labeled assays (e.g., labeled immunoassays) such as, for example, induced luminescence (luminescent oxygen channeling) assays, fluorescent oxygen channeling assays, enzyme-labeled assays, fluorescence polarization assays, radio-labeled assays and inhibition assays.

The sps member may be a label, which is part of a signal producing system. The nature of the label is dependent on the particular assay format as discussed above. A signal producing system may include one or more components, at least one component being a detectable label, which generates a detectable signal that relates to one or both of the amount of bound and unbound label, i.e. the amount of label bound or not bound to analyte being detected or to an agent that reflects the amount of the analyte to be detected. The label is any molecule that produces or can be induced to produce a signal, and may be, for example, a fluorescer, radiolabel, enzyme, chemiluminescer or photosensitizer. Thus, the signal is detected and/or measured by detecting enzyme activity, luminescence, light absorbance or radioactivity, for example, as the case may be.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol; sensitizers including photosensitizers; coenzymes; enzyme substrates; radiolabels such as $^{125}I$, $^{131}I$, $^{14}C$, $^{3}H$, $^{57}Co$ and $^{75}Se$; particles such as latex particles, carbon particles, metal particles including magnetic particles, e.g., chromium dioxide ($CrO_2$) particles, and the like; metal sols; crystallite; liposomes; nucleotides and cells, for example, which may be further labeled with a dye, catalyst or other detectable group.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include, for example, substrates, coenzymes, enhancers, additional enzymes, substances that react with enzymic products, catalysts, activators, cofactors, inhibitors, scavengers, metal ions, and a specific binding substance required for binding of signal generating substances.

As mentioned above, in the present compositions the sps member is associated with the support. The manner of association of the sps member with the solid support depends on one or more of the nature of the support, the nature of the sps member, the surface area and porosity of the support and the nature of any solvent employed, for example. The association may be by adsorption of the sps member by the support, covalent bonding of the sps member to the support, dissolution or dispersion of the sps member in the solid support, non-covalent bonding of the sps member to the support by means of binding pair members (e.g., avidin-biotin and digoxin-antibody for digoxin), for example. In this manner the sps member is "associated with" the solid support.

As used herein, the phrase "associated with" includes covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

Association of an sps member such as, for example, a sensitizer or a chemiluminescent compound, with latex particles may involve incorporation during formation of the particles by polymerization, or incorporation into preformed particles, e.g., by non-covalent dissolution into the particles, for example. In some approaches a solution of the sps member is employed. Solvents that may be utilized include, for example, alcohols, including, e.g., ethanol, ethoxyethanol, methoxyethanol, ethylene glycol and benzyl alcohol; amides such as, e.g., dimethyl formamide, formamide, acetamide and tetramethyl urea; sulfoxides such as, e.g., dimethyl sulfoxide and sulfolane; and ethers such as, e.g., carbitol, ethyl carbitol and dimethoxy ethane; and water; and mixtures of two or more of the above. The use of solvents having high boiling points in which the particles are insoluble permits the use of elevated temperatures to facilitate dissolution of the compounds into the particles and are particularly suitable. The solvents may be used singly or in combination. A solvent should be selected that does not interfere with the signal producing ability of the sps members because of their intrinsic properties or ability to be removed from the particles. In some embodiments aromatic solvents may be employed such as, for example, dibutylphthalate, benzonitrile, naphthonitrile, dioctylterephthalate, dichlorobenzene, diphenylether and dimethoxybenzene.

Generally, the temperature employed during the procedure is chosen to maximize the amount of signal from the sps member particles with the proviso that the particles should not melt or become aggregated at the selected temperature. In some embodiments, elevated temperatures are employed. The temperatures for the procedure may range from about 20° C. to about 200° C., or from about 50° C. to about 170° C. It has been observed that some compounds that are nearly insoluble at room temperature are soluble in, for example, low molecular weight alcohols, such as ethanol and ethylene glycol, for example, at elevated temperatures. Carboxylated modified latex particles have been shown to tolerate low molecular weight alcohols at such temperatures.

In some embodiments of the present compositions, the sps member is selected from the group consisting of sensitizers, including photosensitizers, and chemiluminescent compounds as discussed more fully hereinbelow.

A chemiluminescent compound (chemiluminescer) is a compound that is chemically activatable and, as a result of such activation, emits light at a certain wavelength. Examples of chemiluminescers, by way of illustration and not limitation, include olefins capable of reacting with singlet oxygen or a peroxide to form hydroperoxides or dioxetanes, which can decompose to ketones or carboxylic acid derivatives; stable dioxetanes which can decompose by the action of light; acetylenes which can react with singlet oxygen to form diketones; hydrazones or hydrazides that can form azo compounds or azo carbonyls such as luminol; and aromatic compounds that can form endoperoxides, for example. As a consequence of the activation reaction, the chemiluminescers directly or indirectly cause the emission of light.

A sensitizer is a molecule, usually a compound, for generation of a reactive intermediate such as, for example, singlet oxygen, for activation of a chemiluminescent compound. In some embodiments of the present compositions, the sensitizer is a photosensitizer. Other sensitizers that can be chemiactivated (by, e.g., enzymes and metal salts) include, by way of example and not limitation, other substances and compositions that can produce singlet oxygen with or, less preferably, without activation by an external light source. For example, certain compounds have been shown to catalyze the conversion of hydrogen peroxide to singlet oxygen and water.

Also included within the scope of photosensitizers are compounds that are not true sensitizers but which on excitation by heat, light, ionizing radiation, or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

A photosensitizer is a sensitizer for activation of a photoactive compound, for example, by generation of singlet oxygen by excitation with light. The photosensitizers are photoactivatable and include, e.g., dyes and aromatic compounds, and are usually compounds comprised of covalently bonded atoms, usually with multiple conjugated double or triple bonds. The compounds should absorb light in the wavelength range of 200 to 1,100 nm, or 300 to 1,000 nm, or 450 to 950 nm, with an extinction coefficient at its absorbance maximum greater than 500 $M^{-1} cm^{-1}$, or greater than 5,000 $M^{-1} cm^{-1}$, or greater than 50,000 $M^{-1} cm^{-1}$, at the excitation wavelength. Photosensitizers should be relatively photostable and, preferably, not react efficiently with singlet oxygen. Examples of photosensitizers, by way of illustration and not limitation, include acetone, benzophenone, 9-thioxanthone, eosin, 9,10-dibromoanthracene, methylene blue, metallo-porphyrins, such as hematoporphyrin, phthalocyanines, chlorophylls, rose bengal, and buckminsterfullerene, for example, and derivatives of these compounds.

Examples of chemiluminescent compounds and photosensitizers that may be utilized in embodiments of the present compositions are set forth in U.S. Pat. No. 5,340,716 (Ullman, et al.), the relevant portions of which disclosure are incorporated herein by reference.

In some embodiments the pendant moiety of the polymerized monomer (first polymerized monomer) that comprises an aldehyde or an aldehyde derivative is

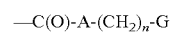

wherein:

A is O or $NR^1$ wherein $R^1$ is H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example;

n is 1 to 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example; and G is CHO; $CH(OR^8)_2$ wherein $R^8$ is alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example; COOH or a derivative there of such as, e.g., an ester or an amide; $NR^1$ wherein $R^1$ is H or alkyl of from 1 to 6 carbon atoms; a member of a specific binding pair.

In some embodiments the pendant moiety of the polymerized monomer that comprises at least 1 carbon atom and at least 2 heteroatoms has the formula:

(i) —COOR$^{10}$ wherein R$^{10}$ is H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example;

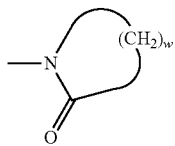

(ii)

wherein: w is 2-4, or 2-3, or 3-4, or 2, or 3, or 4; or (iii) —C(O)—X—(CH$_2$)$_p$—(Y)$_q$—(CH$_2$)$_r$—Z wherein:

X is O or NR$^2$ wherein R$^2$ is H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example;

Y is —(CH$_2$O)$_m$— wherein m is 1 to 100, or 2 to 100, or 3 to 100, or 4 to 100, or 1 to 90, or 1 to 80, or 1 to 70, or 1 to 60, or 1 to 50, 1 to 40, or 1 to 30, or 1 to 20, or 1 to 10, or 1 to 5, or 5 to 100, or 5 to 90, or 5 to 80, or 5 to 70, or 5 to 60, or 5 to 50, 5 to 40, or 5 to 30, or 5 to 20, or 5 to 10, or 10 to 100, or 10 to 90, or 10 to 80, or 10 to 70, or 10 to 60, or 10 to 50, or 10 to 40, or 10 to 30, or 10 to 20, for example; or ⊕N$^⊕$(R$^3$R$^4$) wherein R$^3$ and R$^4$ are independently H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example;

p is 0 to 10, or 0 to 9, or 0 to 8, or 0 to 7, or 0 to 6, or 0 to 5, or 0 to 4, or 0 to 3, or 0 to 2, or 0 to 1, or 1 to 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, being at least 1 when Y is ⊕N$^⊕$(R$^3$, R$^4$);

q is 0 or 1;

r is 0 to 10, or 0 to 9, or 0 to 8, or 0 to 7, or 0 to 6, or 0 to 5, or 0 to 4, or 0 to 3, or 0 to 2, or 0 to 1, or 1 to 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, being at least 1 when Y is ⊕N$^⊕$(R$^3$, R$^4$); and Z is SO$_3^-$; alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example; —(CHOH)$_t$(CH$_2$)$_u$CH$_3$ wherein t is 1 to 5, 1 to 4, or 1 to 3, or 1 to 2, or 2 to 5, or 2 to 4, or 2 to 3, or 3 to 5, or 3 to 4, or 4 to 5, for example, and u is 0 to 10, or 0 to 9, or 0 to 8, or 0 to 7, or 0 to 6, or 0 to 5, or 0 to 4, or 0 to 3, or 0 to 2, or 0 to 1, or 1 to 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example.

In some embodiments the pendant moiety comprises about 4 carbon atoms and about 3 heteroatoms. In some embodiments the pendant moiety comprises about 8 carbon atoms and about 7 heteroatoms. In some embodiments the pendant moiety comprises about 4 carbon atoms and about 2 heteroatoms. In some embodiments the pendant moiety comprises 1 carbon atom and about 2 heteroatoms.

General Description of Assays in which the Present Compositions May be Utilized

The following discussion is by way of illustration and not limitation. The present compositions may be employed in any assay that employs a particle reagent. The present compositions have particular application to assays in which a polymer coated particle is utilized where the uncoated particle has a hydrophobic surface. The assays can be performed either without separation (homogeneous) or with separation (heterogeneous) of any of the assay components or products. Heterogeneous assays usually involve one or more separation steps and can be competitive or non-competitive.

Immunoassays may involve labeled or non-labeled reagents. Immunoassays involving non-labeled reagents usually comprise the formation of relatively large complexes involving one or more antibodies. Such assays include, for example, immunoprecipitin and agglutination methods and corresponding light scattering techniques such as, e.g., nephelometry and turbidimetry, for the detection of antibody complexes. Labeled immunoassays include chemiluminescence immunoassays, enzyme immunoassays, fluorescence polarization immunoassays, radioimmunoassay, inhibition assay, induced luminescence, fluorescent oxygen channeling assay, and so forth.

One general group of immunoassays in which embodiments of the present compositions may be employed to determine the presence and/or amount of and analyte in a sample includes immunoassays using a limited concentration of one of the assay reagents. Another group of immunoassays involves the use of an excess of one or more of the principal reagents. Another group of immunoassays are separation-free homogeneous assays in which the labeled reagents modulate the label signal upon binding of the present composition and an analyte in the sample.

In a typical competitive heterogeneous assay, an embodiment of the present composition that comprises an sbp member that binds to an analyte is contacted with a medium containing the sample suspected of containing the analyte and the analyte conjugated to a label that is reactive with the sps member of the present composition or with a product of the activation of the sps member. Activation of the sps member on the present composition produces a signal from the label if the analyte is present, which is determined by conventional techniques and is related to the amount of the analyte in the sample.

In a typical non-competitive sandwich assay, an immune sandwich complex is formed in an assay medium. The complex comprises the analyte, an sbp member (first sbp member) of the present compositions and a second sbp member that binds to the analyte or to the first sbp member. Subsequently, the immune sandwich complex is detected and is related to the amount of analyte in the sample. The immune sandwich complex is detected by virtue of the presence in the complex of one or more of a label of the present composition and a label of the second sbp member.

Some known assays utilize a signal producing system that employs first and second sps members. The sps members may be related in that activation of one member of the sps produces a product such as, e.g., light, which results in activation of another member of the sps.

In one approach in a sandwich assay, a first incubation of the present composition is contacted with a medium containing a sample suspected of containing the analyte. After a wash and separation step, the support of the present composition is contacted with a medium containing a second sbp member such as, for example, an antibody for the analyte, which contains a label such as an enzyme, for a second incubation period. The labels are related in that activation of one of the labels activates the other label if the analyte is present in the medium. The support is again washed and separated from the medium and either the medium or the support is examined for the presence of a signal. The presence and amount of signal is related to the presence or amount of the analyte.

In a variation of the above sandwich assay, the sample suspected of containing the analyte in a suitable medium is contacted with labeled antibody for the analyte and incubated for a period of time. Then, the medium is contacted with the present composition, which comprises a label that is related to the label of the labeled antibody as discussed above. After an incubation period, the support is separated from the medium and washed to remove unbound reagents. The support or the medium is examined for the presence of a signal, which is related to the presence or amount of analyte. In another variation of the above, the sample, the present composition and the labeled antibody are combined in a medium and incubated in a single incubation step. Separation, wash steps and examination for signal are as described above.

In some embodiments of known assays, the sps members comprise a sensitizer such as, for example, a photosensitizer, and a chemiluminescent composition where activation of the sensitizer results in a product that activates the chemiluminescent composition. The second sps member usually generates a detectable signal that relates to the amount of bound and/or unbound sps member, i.e. the amount of sps member bound or not bound to the analyte being detected or to an agent that reflects the amount of the analyte to be detected. In accordance with embodiments of the present invention, the present composition may comprise one of either the sensitizer reagent or the chemiluminescent reagent.

In an embodiment of such an assay, an induced luminescence immunoassay may be employed where the assay utilizes a composition in accordance with the present embodiments, which includes a sensitizer or a chemiluminescent compound as the sps member of the composition. The induced luminescence immunoassay is referred to in U.S. Pat. No. 5,340,716 (Ullman), which disclosure is incorporated herein by reference. In one approach in accordance with the present embodiments, the assay uses a particle coated with a copolymer in accordance with the present embodiments and having associated therewith a photosensitizer and a first sbp member. The chemiluminescent reagent comprises a second sbp member. The sbp members bind to the analyte to form a complex, or the first sbp member binds to the second sbp member to form a complex, in relation to the presence of the analyte in the medium. If the analyte is present, the photosensitizer and the chemiluminescent compound come into close proximity by virtue of the binding based on the presence of the analyte. The photosensitizer generates singlet oxygen and activates the chemiluminescent reagent when the two labels are in close proximity. The activated chemiluminescent reagent subsequently produces light. The amount of light produced is related to the amount of the complex formed, which in turn is related to the amount of analyte present.

In some embodiments of the induced luminescence assay, a photosensitizer particle is employed that is conjugated to avidin or streptavidin. A biotinylated sbp member that binds to the analyte is also employed. An embodiment of the present compositions is employed where the sps member is a chemiluminescent reagent and the sbp member binds to the analyte is employed as part of the detection system. The reaction medium is incubated to allow the photosensitizer particles to bind to the biotinylated sbp member by virtue of the binding between avidin and biotin and to also allow the binding partner for the analyte that is part of the present composition to bind to the analyte. Then, the medium is irradiated with light to excite the photosensitizer, which is capable in its excited state of activating oxygen to a singlet state. Because the chemiluminescent reagent is now in close proximity to the photosensitizer by virtue of the presence of the analyte, it is activated by the singlet oxygen and emits luminescence. The medium is then examined for the presence and/or the amount of luminescence or light emitted, the presence thereof being related to the presence and/or amount of the analyte.

The concentration of the analyte that may be assayed generally varies from about $10^{-5}$ to about $10^{-17}$ M, or from about $10^{-6}$ to about $10^{-14}$ M. Considerations, such as whether the assay is qualitative, semi-quantitative or quantitative (relative to the amount of the analyte present in the sample), the particular detection technique and the expected concentration of the analyte normally determine the concentrations of the various reagents.

The concentrations of the various reagents in the assay medium will generally be determined by the concentration range of interest of the analyte, the nature of the assay, and the like. However, the final concentration of each of the reagents is normally determined empirically to optimize the sensitivity of the assay over the range. That is, a variation in concentration of analyte that is of significance should provide an accurately measurable signal difference. Considerations such as the nature of the signal producing system and the nature of the analytes, for example, determine the concentrations of the various reagents.

As mentioned above, the sample and reagents are provided in combination in the medium. While the order of addition to the medium may be varied, there will be certain preferences for some embodiments of the assay formats described herein. The simplest order of addition, of course, is to add all the materials simultaneously and determine the effect that the assay medium has on the signal as in a homogeneous assay. Alternatively, each of the reagents, or groups of reagents, can be combined sequentially. In some embodiments, an incubation step may be involved subsequent to each addition as discussed above. In heterogeneous assays, washing steps may also be employed after one or more incubation steps.

Assay Methods Utilizing Embodiments of the Present Compositions

As mentioned above, an embodiment of the present invention is a method of determining one or more of the presence and amount of an analyte in a sample. The analyte is a substance of interest or the compound or composition to be detected and/or quantitated. Analytes include, for example, drugs, metabolites, pesticides and pollutants. Representative analytes, by way of illustration and not limitation, include alkaloids, steroids, lactams, aminoalkylbenzenes, benzheterocyclics, purines, drugs derived from marijuana, hormones, polypeptides which includes proteins, immunosuppressants, vitamins, prostaglandins, tricyclic antidepressants, anti-neoplastics, nucleosides and nucleotides including polynucleosides and polynucleotides, miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, and metabolites and derivatives of all of the above. Also included are metabolites related to disease states, aminoglycosides, such as gentamicin, kanamicin, tobramycin, and amikacin, and pesticides such as, for example, polyhalogenated biphenyls, phosphate esters, thiophosphates, carbamates and polyhalogenated sulfenamides and their metabolites and derivatives. The term analyte also includes combinations of two or more of polypeptides and proteins, polysaccharides and nucleic acids. Such combinations include, for example, components of bacteria, viruses, chromosomes, genes, mitochondria, nuclei and cell membranes. Protein analytes include, for example, immunoglobulins, cytokines, enzymes, hormones, cancer antigens, nutritional markers and tissue specific antigens. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, α-fetoprotein, acid phosphatase, CA19.9, CA15.3 and CA125, tissue specific antigens, such as, e.g., alkaline phosphatase, myoglobin, CPK-MB and calcitonin, and peptide hormones. Other polymeric materials of interest are mucopolysaccharides and polysaccharides. As indicated above, the term analyte further includes oligonucleotide and polynucleotide analytes such as m-RNA, r-RNA, t-RNA, DNA and DNA-RNA duplexes, for example.

The sample to be tested may be non-biological or biological. "Non-biological samples" are those that do not relate to a biological material and include, for example, soil samples, water samples and mineral samples. The phrase "biological sample" refers to any biological material such as, for example, body fluid, tissue and the like, which is obtained from the body of a mammal. Body fluids include, for example, whole-blood, plasma, serum, interstitial fluid, sweat, saliva, urine, semen, blister fluid, inflammatory exudates, stool, sputum, cerebral spinal fluid, tears, mucus, lymphatic fluid, vaginal mucus, and the like. The biological tissue includes excised tissue from an organ or other body part of a host, e.g., tissue biopsies; hair and skin; and so forth.

The method comprises providing in combination in a medium the sample, which may or may not be pretreated, and an embodiment of the present composition, which comprises an sbp member associated with the support. The sbp member binds to the analyte or to a second sbp member to form a complex related to the presence of the analyte. An sbp member is one of two different molecules, having an area on the surface or in a cavity, which specifically binds to and is thereby defined as complementary with a particular spatial and polar organization of the other molecule. The sbp members will usually be members of an immunological pair such as antigen-antibody, although other specific binding pairs such as biotin-avidin, hormones-hormone receptors, enzyme-substrate, nucleic acid duplexes, IgG-protein A, polynucleotide pairs such as DNA-DNA, DNA-RNA, for example, are not immunological pairs but are included within the scope of the phrase sbp member. In some embodiments, depending on the nature of the assay to be conducted as explained more fully below, other reagents are included in the medium such as, for example, other sbp members and other sps members.

The sample can be prepared in any convenient medium. For example, the sample may be prepared in an assay medium, which is discussed more fully hereinbelow. In some instances a pretreatment may be applied to the sample such as, for example, to lyse blood cells. Such pretreatment is usually performed in a medium that does not interfere subsequently with an assay. An aqueous medium is preferred for the pretreatment.

The sbp member is associated with the support of the composition. In some embodiments the sbp member is covalently linked to the copolymer coated on the solid support. In some embodiments the copolymer is covalently linked to the aldehyde bearing site of the copolymer coating the solid support.

An assay medium, which in some embodiments is an aqueous buffered medium at a moderate pH, is generally one that which provides optimum assay sensitivity. The aqueous medium may be solely water or may include from 0.1 to about 40 volume percent of a cosolvent such as, for example, a water miscible organic solvent, e.g., an alcohol, an ether or an amide. The pH for the medium will usually be in the range of about 4 to about 11, or in the range of about 5 to about 10, or in the range of about 6.5 to about 9.5, for example. The pH utilized is often the result of a compromise between optimum binding of the binding members of any specific binding pairs and the pH optimum for other reagents of the assay such as members of the signal producing system, for example. Various buffers may be used to achieve the desired pH and maintain the pH during the determination. Illustrative buffers include borate, phosphate, carbonate, tris, barbital, PIPES, HEPES, MES, ACES, MOPS, BICINE, and the like. The particular buffer employed is not critical, but in an individual assay one or another buffer may be preferred.

Various ancillary materials may be employed in the assay methods. For example, in addition to buffers the medium may comprise stabilizers for the medium and for the reagents employed. In some embodiments, in addition to these additives, the medium may include proteins such as, e.g., albumins; organic solvents such as, e.g., formamide; quaternary ammonium salts; polyanions such as, e.g., dextran sulfate; binding enhancers, e.g., polyalkylene glycols; polysaccharides such as, e.g., dextran, trehalose, or the like. The medium may also comprise agents for preventing the formation of blood clots. Such agents are well known in the art and include, for example, EDTA, EGTA, citrate and heparin. The medium may also comprise one or more preservatives as are known in the art such as, for example, sodium azide, neomycin sulfate, PROCLIN® 300 and Streptomycin. Any of the above materials, if employed, is present in a concentration or amount sufficient to achieve the desired effect or function.

As mentioned above, depending on the nature of the assay employed, the medium may further comprise one or more components such as, for example, a small molecule, an additional particle, an additional sps members and additional binding agents such as one or more sbp members (e.g., antibodies), which are different from those that are part of the present composition. Furthermore, again depending on the nature of the assay employed, other reagents may also be included in the initial combination or added subsequently.

The combination is subjected to conditions for binding of the analyte to the composition to form a complex. Such conditions may include one or more incubation periods that may be applied to the medium at one or more intervals including any intervals between additions of various reagents employed in an assay including those mentioned above, some or all of which may be in the initial combination. The medium is usually incubated at a temperature and for a time sufficient for binding of various components of the reagents and binding between complementary sbp members such as, for example, an analyte and a complementary sbp member or first and second sbp members to occur. Moderate temperatures are normally employed for carrying out the method and usually constant temperature, preferably, room temperature, during the period of the measurement. In some embodiments incubation temperatures range from about 5° to about 99° C., or from about 15° C. to about 70° C., or from about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The time period depends on the temperature of the medium and the rate of binding of the various reagents, which is determined by one or more of the association rate constant, the concentration, the binding constant and dissociation rate constant, for example.

Following the above incubation periods, if any, the sps member is activated and the amount of the complex formed between the analyte and an sbp member or between an sbp member and an sbp member that is indicative of the analyte is detected. The amount of the complex is related to one or both of the presence and amount of analyte in the sample. The detection of the complex is dependent on the nature of the assay being performed, the nature of the sps members, and the nature of the sbp members, for example.

In an embodiment, the present invention is a method of determining in a sample one or more of the presence and amount of an analyte. A combination is provided in a medium. The combination comprises the sample and a composition comprising a particle comprising a member of a signal producing system, a member of the specific binding pair that binds to the analyte or to a second sbp member to form a complex related to the presence of the analyte and a coating of a copolymer. The copolymer has the formula:

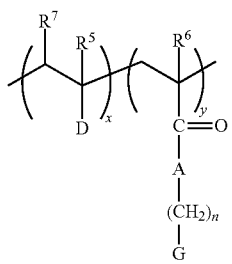

wherein: D is (i) —COOR$^{10}$ wherein R$^{10}$ is H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example;

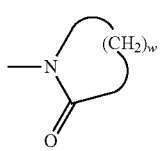

wherein:

w is as defined above; or (iii) —C(O)—X—(CH$_2$)$_p$—(Y)$_q$—(CH$_2$)$_r$—Z wherein:

A, R$^1$, n, G, R$^8$, X, R$^2$, Y, m, R$^3$, R$^4$, p, q, r, Z, t and u are as defined above;

R$^5$, R$^6$ and R$^7$ are independently H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example; and x and y are independently 1 to about 1000, or 1 to about 800, or 1 to about 600, or 1 to about 400, or 1 to about 200, or 1 to about 100, or about 5 to about 1000, or about 5 to about 800, or about 5 to about 600, or about 5 to about 400, or about 5 to about 200, or about 5 to about 100, or about 10 to about 1000, or about 10 to about 800, or about 10 to about 600, or about 10 to about 400, or about 10 to about 200, or about 10 to about 100, or about 50 to about 1000, or about 50 to about 800, or about 50 to about 600, or about 50 to about 400, or about 50 to about 200, or about 50 to about 100, or about 100 to about 1000, or about 100 to about 800, or about 100 to about 600, or about 100 to about 400, or about 100 to about 200, for example.

The combination is subjected to conditions for binding of the member of the specific binding pair to the analyte or to the second specific binding pair member to form a complex. The member of the signal producing system is activated and the amount of the complex is detected. The amount of the complex is related to one or more of the presence and amount of analyte in the sample.

In some embodiments of the above method, the member of the signal producing system of the present compositions is a photosensitizer and the combination further comprises a chemiluminescent reagent that comprises a particle having a chemiluminescent compound associated therewith and having a coating of a copolymer of the formula:

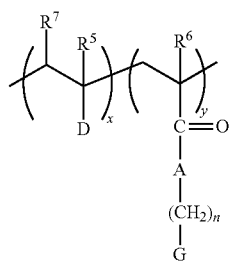

wherein:

D is (i) —COOR$^{10}$ wherein R$^{10}$ is as defined above;

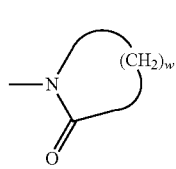

wherein:
w is as defined above; or
(iii) —C(O)—X—(CH$_2$)$_p$—(Y)$_q$(CH$_2$)$_r$—Z'
wherein:
A, R$^1$, n, G, R$^8$, X, R$^2$, Y, m, R$^3$, R$^4$, p, q, r, t, u, R$^5$, R$^6$, R$^7$, x and y are as defined above;
and
Z' is SO$_3^-$; or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example.

In some embodiments of the above method, the member of the signal producing system of the present compositions is a chemiluminescent compound and the combination further comprises a photosensitizer reagent that comprises a particle having a photosensitizer associated therewith and having a coating of a copolymer of the formula:

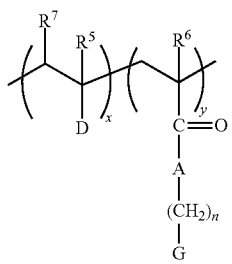

wherein:
D is
(i) —COOR$^{10}$ wherein R$^{10}$ is as defined above;

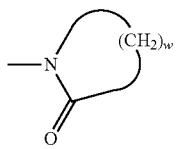

wherein:
w is as defined above; or
(iii) —C(O)—X—(CH$_2$)$_p$—(Y)$_q$(CH$_2$)$_r$—Z'
wherein:
A, R$^1$, n, G, R$^8$, X, R$^2$, Y, m, R$^3$, R$^4$, p, q, r, t, u, R$^5$, R$^6$, R$^7$, x and y are as defined above;
and
Z' is SO$_3^-$; or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example.

Examination Step

In a next step of an assay method, the medium is examined for the presence of a complex comprising the analyte. One or both of the presence and amount of the complex indicates one or both of the presence and amount of the analyte in the sample.

The phrase "measuring the amount of analyte" refers to the quantitative, semiquantitative and qualitative determination of the analyte. Methods that are quantitative, semiquantitative and qualitative, as well as all other methods for determining the analyte, are considered to be methods of measuring the amount of the analyte. For example, a method, which merely detects the presence or absence of the analyte in a sample suspected of containing the analyte, is considered to be included within the scope of assays in which the present compositions may be utilized. The terms "detecting" and "determining," as well as other common synonyms for measuring, are contemplated within the scope of assay methods.

In many embodiments the examination of the medium involves detection of a signal from the medium. One or both of the presence and amount of the signal is related to one or both of the presence and amount of the analyte in the sample. The particular mode of detection depends on the nature of the signal producing system. As discussed above, there are numerous methods by which a label of a signal producing system can produce a signal detectable by external means. Activation of a signal producing system depends on the nature of the signal producing system members.

Temperatures during measurements generally range from about 10° to about 70° C., or from about 20° to about 45° C., or about 20° to about 25° C., for example. In one approach standard curves are formed using known concentrations of the analyte. Calibrators and other controls may also be used.

Luminescence or light produced from any label can be measured visually, photographically, actinometrically, spectrophotometrically or by any other convenient means to determine the amount thereof, which is related to the amount of analyte in the medium. The examination for one or both of the presence and amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, or chemiluminometer, for example.

Kits Comprising Reagents for Conducting Assays

Embodiments of the present compositions and other reagents for conducting a particular assay for an analyte may be present in a kit useful for conveniently performing an assay for the determination of an analyte. In some embodiments a kit comprises in packaged combination a composition in accordance with the present embodiments wherein the sbp member is an antibody for an analyte and the sps member is a photosensitizer or a chemiluminescent compound. In some embodiments, depending on the sps member of the present compositions, the kit also includes a photosensitizer or a chemiluminescent compound associated with an sbp member for the analyte. The kit may further include other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional sbp members, sps members and ancillary reagents, for example.

The relative amounts of the various reagents in the kits can be varied widely to provide for concentrations of the reagents that substantially optimize the reactions that need to occur during the present methods and further to optimize substantially the sensitivity of an assay. Under appropriate circumstances one or more of the reagents in the kit can be provided as a dry powder, usually lyophilized, including excipients, which on dissolution will provide for a reagent solution having the appropriate concentrations for performing a method or assay utilizing embodiments of the present compositions. The kit can further include a written description of a method as described above.

Embodiments of Copolymers

The following embodiments of copolymers are by way of illustration and not limitation.

In some embodiments a copolymer has the formula:

$$\left(\begin{array}{c}R^7\\|\\\phantom{X}\\D'\end{array}\right)_x \left(\begin{array}{c}R^5\\|\\\phantom{X}\end{array}\right) \left(\begin{array}{c}R^6\\|\\C=O\\|\\A\\|\\(CH_2)_n\\|\\G'\end{array}\right)_y$$

wherein:

A is O or $NR^1$ wherein $R^1$ is H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example;

n is 1 to 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example; and G' is CHO; $CH(OR^8)_2$ wherein $R^8$ is alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example; a member of a specific binding pair;

D' is (i) —$COOR^{10}$ wherein $R^{10}$ is H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example;

(ii)

$$-N\underset{O}{\overset{(CH_2)_w}{\diagup\!\!\!\diagdown}}$$

wherein:

w is 2-4, or 2-3, or 3-4, or 2, or 3, or 4; or (iii) —C(O)—X—$(CH_2)_p$—$(Y)_q$—$(CH_2)_r$—Z' wherein:

X is O or $NR^2$ wherein $R^2$ is H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example;

Y is —$(CH_2O)_m$— wherein m is 1 to 100, or 2 to 100, or 3 to 100, or 4 to 100, or 1 to 90, or 1 to 80, or 1 to 70, or 1 to 60, or 1 to 50, 1 to 40, or 1 to 30, or 1 to 20, or 1 to 10, or 1 to 5, or 5 to 100, or 5 to 90, or 5 to 80, or 5 to 70, or 5 to 60, or 5 to 50, 5 to 40, or 5 to 30, or 5 to 20, or 5 to 10, or 10 to 100, or 10 to 90, or 10 to 80, or 10 to 70, or 10 to 60, or 10 to 50, or 10 to 40, or 10 to 30, or 10 to 20, for example; or $\oplus N^{\oplus}(R^3R^4)$ wherein $R^3$ and $R^4$ are independently H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example;

p is 0 to 10, or 0 to 9, or 0 to 8, or 0 to 7, or 0 to 6, or 0 to 5, or 0 to 4, or 0 to 3, or 0 to 2, or 0 to 1, or 1 to 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, being at least 1 when Y is $\oplus N^{\oplus}(R^3, R^4)$;

q is 0 or 1;

r is 0 to 10, or 0 to 9, or 0 to 8, or 0 to 7, or 0 to 6, or 0 to 5, or 0 to 4, or 0 to 3, or 0 to 2, or 0 to 1, or 1 to 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, being at least 1 when Y is $\oplus N^{\oplus}(R^3, R^4)$; and Z' is $SO_3^-$; alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example;

$R^5$, $R^6$ and $R^7$ are independently H or alkyl of from 1 to 6, or 1 to 5, or 1 to 4, or 1 to 3, or 1 to 2, or 2 to 6, or 2 to 5, or 2 to 4, or 2 to 3, or 3 to 6, or 3 to 5, or 3 to 4, or 4 to 6, or 4 to 5, or 5 to 6 carbon atoms, for example; and x and y are independently 1 to about 1000, or 1 to about 800, or 1 to about 600, or 1 to about 400, or 1 to about 200, or 1 to about 100, or about 5 to about 1000, or about 5 to about 800, or about 5 to about 600, or about 5 to about 400, or about 5 to about 200, or about 5 to about 100, or about 10 to about 1000, or about 10 to about 800, or about 10 to about 600, or about 10 to about 400, or about 10 to about 200, or about 10 to about 100, or about 50 to about 1000, or about 50 to about 800, or about 50 to about 600, or about 50 to about 400, or about 50 to about 200, or about 50 to about 100, or about 100 to about 1000, or about 100 to about 800, or about 100 to about 600, or about 100 to about 400, or about 100 to about 200, for example.

In some embodiments of the above copolymer:

A is $NR^1$ wherein $R^1$ is as defined above;

n, G, $R^8$, $R^5$, $R^6$, $R^7$, x and y are as defined above;

D' is —C(O)—X—$(CH_2)_p$—$(Y)_q$—$(CH_2)_r$—Z' wherein:

X is O;

Y is $\oplus N^{\oplus}(R^3R^4)$ wherein $R^3$ and $R^4$ are as defined above;

p is 1 to 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example;

q is 1;

r is 1 to 10, or 1 to 9, or 1 to 8, or 1 to 7, or 1 to 6, or 1 to 5, 1 to 4, or 1 to 3, or 1 to 2, or 2 to 10, or 2 to 9, or 2 to 8, or 2 to 7, or 2 to 6, or 2 to 5, 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example; and Z' is $SO_3^-$.

In some embodiments of the above copolymer:
A is NH;
n is 1;
G is CHO; CH(OR$^8$)$_2$ wherein R$^8$ is methyl; a member of a specific binding pair;
D' is —C(O)—X—(CH$_2$)$_p$—(Y)$_q$—(CH$_2$)$_r$—Z' wherein:
X is O;
Y is $\oplus$N$^\oplus$(R$^3$R$^4$) wherein R$^3$ and R$^4$ are both methyl;
p is 2;
q is 1;
r is 3;
Z' is SO$_3^-$;
R$^5$ and R$^6$ are independently H or methyl and R$^7$ is H; and
x and y are as defined above.

In some embodiments of the above copolymer:
A is NR$^1$ wherein R$^1$ is as defined above;
n, G, R$^8$, R$^5$, R$^6$, R$^7$, x and y are as defined above;
D' is —C(O)—X—(CH$_2$)$_p$—(Y)$_q$—(CH$_2$)—Z' wherein:
X is O;
Y is —(CH$_2$O)$_m$— wherein m is as defined above;
p is 0;
q is 1;
r is 0; and
Z' is methyl.

In some embodiments of the above copolymer:
A is NH;
n is 1;
G is CHO; CH(OR$^8$)$_2$ wherein R$^8$ is methyl; a member of a specific binding pair;
D' is —C(O)—X—(CH$_2$)$_p$—(Y)$_q$(CH$_2$)$_r$—Z' wherein:
X is O;
Y is —(CH$_2$O)$_m$— wherein m is as defined above;
p is 0;
q is 1;
r is 0;
Z' is methyl;
R$^5$ and R$^6$ are independently H or methyl and R$^7$ is H; and
x and y are as defined above.

In some embodiments of the above copolymer:
A is NR$^1$ wherein R$^1$ is H or alkyl of from 1 to 6 carbon atoms;
n is 1 to 10;
G' is CHO; CH(OR$^8$)$_2$ wherein R$^8$ is alkyl of from 1 to 6 carbon atoms; or a member of a specific binding pair;
D' is —COOH;
R$^5$, R$^6$ and R$^7$ are independently H or alkyl of from 1 to 6 carbon atoms; and
x and y are independently 1 to 1000.

In some embodiments of the above copolymer:
A is NH;
n is 1;
G' is CHO; CH(OR$^8$)$_2$ wherein R$^8$ is methyl; or a member of a specific binding pair;
D' is

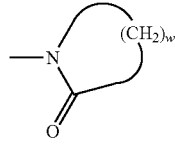

wherein:
w is 3;
R$^5$ and R$^6$ are independently H or methyl and R$^7$ is H; and
x and y are independently 1 to 1000.

Definitions

The following definitions are provided for terms and phrases not otherwise specifically defined above.

The phrase "at least" as used herein means that the number of specified items may be equal to or greater than the number recited.

The phrase "about" as used herein means that the number recited may differ by plus or minus 10%; for example, "about 5" means a range of 4.5 to 5.5.

The designations "first" and "second" are used solely for the purpose of differentiating between two items such as, for example, "first sps member" and "second sps member," or "first polymerized monomer" and "second polymerized monomer" and are not meant to imply any sequence or order or importance to one item over another or any order of addition, for example.

The following examples further describe specific embodiments of the invention by way of illustration and not limitation and are intended to describe and not to limit the scope of the invention. Parts and percentages disclosed herein are by volume unless otherwise indicated.

EXAMPLES

Materials

Unless indicated otherwise, reagents were purchased from Sigma-Aldrich (Milwaukee, Wis.) and used as received unless indicated otherwise.

Abbreviations cTnI cardiac troponin I
cTnI flex FLEX® cartridge of commercial cTnI assay from Siemens
BSA bovine serum albumin
LOCI luminescent oxygen channeling immunoassay
HEPES hydroxyethyl piperazine-ethanesulfonic acid
Wash buffer 50 mM HEPES, pH 8.0
BSA wash buffer 50 mM HEPES-1.0 mg/mL BSA, pH 8.0
HPMA N-2-hydroxypropylmethacrylamide
DMSO dimethylsulfoxide
AIBN azobis(isobutyronitrile)
PEG poly(ethylene glycol)
NaCNBH$_3$ sodium cyanoborohydride
MAMDMA methacrylamidoacetaldehyde dimethyl acetal
THF tetrahydrofuran
HCl hydrochloric acid
NaOH sodium hydroxide
TAPS N-tris-(hydroxymethyl)methyl-3-aminopropylsulfonic acid
TAPS buffer TAPS sodium salt buffer, 50 mM, pH 9.0
MES 2-(N-morpholino)ethanesulfonic acid
MES buffer 50 mM MES buffer, pH 5.0
STUT N,N,N',N'-tetramethyl-O—(N-succinimidyl)-uronium tetrafluoroborate
DMF dimethyl formamide
DMAP 4-N,N-dimethylamino-pyridine
MA.Actl methacrylamidoacetaldehyde
NHA 4,4,5,5,6,6,6-heptafluoro-1-(naphthalene-2-yl)hexane-1,3-dione
DPP 4,7-diphenyl-1,10-phenathroline
C-28 thioxene C-28 thioxene, substituted N-phenyl oxazine and thioxene attached to 9,10-bis(phenylethynyl) anthracene (BPEA) prepared as described in U.S.

Pat. No. 6,406,667, the relevant disclosure of which is incorporated herein by reference hrs hours min minutes DI deionized w/w weight to weight rpm rounds per minute mL milliliters mg milligrams g grams mM millimolar Sensibead latex particle comprising a photosensitizer dye (bis-(trihexyl)-silicon-t-butyl-phthalocyanine) prepared using a method analogous to that described in U.S. Pat. Nos. 6,153,442, 7,022,529, 7,229,842 and U.S. Patent Application Publication No. 20050118727A, the relevant disclosures of which are incorporated herein by reference Chemibead latex particle comprising a chemiluminescent compound (mixture of europium NHA DPP and C-28 thioxene) prepared in a manner such as described in U.S. Pat. No. 5,811,311, the relevant disclosure of which is incorporated herein by reference.

Preparation of Reagents

Synthesis of MAMDMA (FIG. 1):

Methacrylic acid (9.0 g, 0.1 mole) and N-hydroxysuccinimide (11.5 g, 0.1 mole) were placed in a round bottom flask and dissolved in 300 mL of THF. The solution was cooled in an ice bath. Dicyclohexyl carbodiimide (21.0 g, 0.1 mole) dissolved in 50 mL THF was added. The reaction mixture was stirred for 2 hrs in an ice bath. Aminoacetaldehyde dimethyl acetal (15.0 g, 0.1 mole) and triethylamine (15.0 g, 0.15 mole) were added. The reaction mixture solidified to a cake and became difficult to stir due to this addition. An additional 300 mL THF was added. The reaction mixture was warmed up to room temperature and stirred for 3 days. Reaction mixture was filtered to remove precipitated solids. The clear solution was concentrated under reduced pressure. MAMDMA was obtained as a viscous liquid. Yield: 20.0 g, 90%. $^1$H NMR (CDCl$_3$): 5.4 δ 1H, 5.6 δ 1H (double bond protons), 3.5 δ 6H (acetal protons) 3.1 δ 1H (—CH—(OCH$_3$)$_2$), 2.5 δ 2H (—CH$_2$—CH—), 2.3 δ 1H (—NH—), 1.8 δ 3H (=C—CH$_3$).

Procedure for Polymerization of MAMDMA with a Variety of Hydrophilic Monomers (FIG. 2):

In a round bottom flask equipped with Argon gas inlet and outlet, MAMDMA (0.01M), hydrophilic monomer (0.01 mole) and AIBN (0.0001 mole, [Monomer]/[AIBN]=200) were dissolved in 30 mL DMSO. Argon gas was purged through the DMSO solution at room temperature for 30 min. The flask containing monomer solution was immersed in oil bath pre-heated to 80° C. Polymerization was conducted at 80° C. for 16 hrs under Argon purging. DMSO solution was poured into 700 mL diethyl ether to precipitate the polymer. The polymer was dissolved in 100 mL water and concentrated to 10-15 mL using an ultrafiltration membrane of molecular weight cut off 5,000 daltons.

Procedure for Hydrolysis of Acetal Groups to Obtain Aldehyde Containing Synthetic Copolymers:

An aqueous solution (100 mL) containing 2-3 g copolymer synthesized as above was taken in an Erlenmeyer flask. To this, 100 mL 1N HCl was added. The acidic solution was stirred for 2 days at room temperature; pH of the solution was adjusted to 5.0 with the addition of concentrated NaOH. Presence of aldehyde groups in the copolymer was qualitatively confirmed by purpald assay (Dickinson, R. G.; Jacobsen, N. W., Chemical Communications, p. 1719 (1970). The copolymer solution was concentrated to 10 mL using an ultrafiltration membrane of molecular weight cut off 5,000 daltons. Aqueous polymer solutions (100-150 mg solids/mL) were stored at 4° C.

Procedure for Preparation of Sensibead Coated with Aldehyde Containing Synthetic Copolymers:

An aqueous solution of aldehyde-containing copolymer (5 mL, pH 5.0, 100-150 mg solids/mL) was taken in a Falcon tube. Solution pH was adjusted to 8.5. To this solution was added 1 mL suspension of hydrazide-coated dyed sensibeads (25 mg/mL solids, pH 9.0). The beads were coated with hydrazide by reaction of beads with hydrazine in the presence of STUT at pH 9.0 in a manner similar to that described below for the coating of chemibeads with hydrazide. The reaction mixture was incubated at 50° C. for 72 hrs with gentle shaking. Polymer-coated beads were washed with water twice by centrifugation at 15,000 rpm for 30 min at 15° C. and then were resuspended in fresh water. Polymer-coated beads were suspended in 2 mL 0.1M acetate buffer pH 5.0. To this, streptavidin (7.0 mg) was added and incubated at room temperature for 30 min. To this, NaCNBH$_3$ (40 mg) was added and incubated at 37° C. for 72 hrs with gentle shaking. Streptavidin-coated beads (sensibeads) were washed with BSA wash buffer twice by centrifugation at 15,000 rpm for 30 min at 15° C. and were resuspended in the buffer. Washed sensibeads were suspended by sonication for 2 minutes at 4° C. using a probe sonicator. Solid contents of sensibeads were determined and adjusted to 10 mg/mL. The streptavidin number per particle was determined from the depletion of fluorescence when different concentrations of particles were incubated with a fixed concentration of the biotin-fluorescein conjugate. Sensibeads were stored at 4° C. at 10 mg/mL concentration until further use. The results are set forth in Table 1.

TABLE 1

| Sensibead No. | Streptavidin No. |
| --- | --- |
| SB 1 | 1150 |
| Poly(HPMA-co-MA-Actl) (1:1) | |
| SB 2 | 5313 |
| Poly(HPMA-co-MA-Actl) (1:2) | |
| SB 3 | 3713 |
| Poly(HPMA-co-MA-Actl) (1:4) | |
| SB 4 | 6274 |
| Poly(sulfobetaine-co-MA-Actl) (1:1) | |
| SB 5 | 1477 |
| Poly(MPEG$_{1100}$-MA-co-MA-Actl) (1:1) | |
| SB 6 | 3211 |
| Poly(AA-co-MA-Actl) (1:1) | |
| SB 7 | 2188 |
| Poly(MPEG$_{300}$-MA-co-MA-Actl) (1:1) | |
| SB 8 | ND |
| Poly(NVP-co-MA-Actl) (1:1) | |

Preparation of Chemibeads Coated with Synthetic Copolymer:

Step 1: Preparation of Hydrazide-Coated Dyed Chemibead:

Chemibead suspension (15 mL, 1.046 g particles) was taken in a round bottom flask. To this, 37 mL 300 mM TAPS buffer pH 9.0 was added to make 20 mg/mL particle suspension. Hydrazine (0.1 mL) was added and pH electrode was dipped in the particle suspension and stirred at room temperature. To this, 100 mg STUT (freshly dissolved in 1 mL DMF) was added followed by addition of 0.25 mL DMF solution of DMAP (100 mg/mL). The reaction mixture was stirred for 10 min and the pH was adjusted to 9.0 with addition of 5 N NaOH. STUT and DMAP addition was repeated 4 times and the particle suspension was stirred for an additional 1 hr.

Hydrazide-coated, dyed chemibeads were washed twice with 1 mM TAPS buffer, pH 9.0, by centrifugation at 15,000 rpm, 30 min and 10° C. and were resuspended in the buffer. Washed particles were suspended in 17 mL 1 mM TAPS buffer pH 9.0. Solids content was 41.23 mg/mL.

Step 2: Preparation of poly(HPMA-co-MA-Actl (1:2)) Coated Dyed Chemibead:

Hydrazide-coated chemibead suspension (0.6 mL, 25 mg beads) from above was taken in a 15 mL Falcon tube. Poly (HPMA-co-MA-Actl (1:2, FIG. 2) (3 mL, pH 5.0, solids content 24.7 mg/mL) was taken in another tube and the pH was adjusted to 8.8. Polymer solution of pH 8.8 and hydrazide-coated bead suspension of pH 9.0 were mixed together and incubated at 37° C. for 50 hrs with gentle shaking. Polymer coated beads (CB 2) were washed twice with 50 mM MES buffer, pH 6.0, by centrifugation at 15,000 rpm, 30 min, 10° C. and were resuspended in the MES buffer. Washed beads were resuspended in 0.25 mL MES buffer by sonication using a probe sonicator.

Step 3: Preparation of Capture Antibody-Coated Chemibead:

cTnI capture antibody was buffer exchanged with 10 mM $PO_4$—300 mM NaCl, pH 7.0 containing 0.2% TWEEN 20®. Concentration of buffer exchanged antibody was 7.7 mg/mL. cTnI capture antibody solution (1 mL, 7.7 mg antibody), poly(HPMA-co-MA-Actl (1:2) coated chemibeads (0.25 mL, 25 mg beads), acetic acid (0.4 μL) were mixed together at 4° C. The mixture had pH 5.7. $NaCNBH_3$ (12 μL, 25 mg/mL) was added and the suspension incubated at 4° C. for 16 hrs with gentle shaking. The particles were then incubated at 37° C. for 24 hrs. Antibody-coated chemibeads were washed twice with wash buffer (pH 8.0) by centrifugation at 15,000 rpm, 30 min, 10° C. and were resuspended in the wash buffer. Washed particles were resuspended in 1 mL BSA wash buffer (pH 8.0) by sonication with a probe sonicator. Solids content was 13.37 mg/mL.

Molecular Weight Characterization of Aldehyde-Containing Synthetic Copolymers:

Polymers were characterized by size exclusion chromatography coupled with light scattering. Data obtained are summarized in Table 2. All synthetic polymers were synthesized by conventional free radical polymerization which is known to produce polymers with a large polydispersity. Data in Table 2 also show that aldehyde-containing copolymers were polydispersed. Peaks mentioned in Table 2 for polymers are not strictly bimodal but rather deconvoluted from a broad Gaussian peak present for each polymer as determined using the software Astra (Wyatt Technology Corporation, Santa Barbara Calif.) from light scattering detector. Molecular weight of predominant peaks in polymer samples varied from 25 kDa to 3300 kDa depending on individual monomer structure and its polymerizability.

TABLE 2

Molecular weight characterization of aldehyde-containing copolymers

| SB No. | Polymer | Peak 1 MW (Da) Polydispersity index % Mass | Peak 2 MW (Da) Polydispersity index % Mass |
|---|---|---|---|
| 1 | Poly(HPMA-co-MA-Actl) (1:1) | 120,200 1.13 29.6 | 40,330 1.10 73.1 |
| 2 | Poly(HPMA-co-MA-Actl) (1:2) | 68,070 1.08 27.1 | 26,940 1.09 72.9 |
| 3 | Poly(HPMA-co-MA-Actl) (1:4) | Not determined. Polymer gelled before performing analysis. | |
| 4 | Poly(sulfobetaine-co-MA-Actl) (1:1) | 467,400 1.44 64.5 | 89,560 1.09 35.5 |
| 5 | Poly($MPEG_{1100}$-MA-co-MA-Actl) (1:1) | 3,353,000 2.12 100 | — — — |
| 6 | Poly(AA-co-MA-Actl) (1:1) | 47,980 1.13 21.4 | 14,200 1.17 78.6 |
| 7 | Poly($MPEG_{300}$-MA-co-MA-Actl) (1:1) | 1,447,000 1.062 100 | — — — |
| 8 | Poly(NVP-co-MA-Actl) (1:1) | 399,200 2.18 26.8 | 38,340 1.09 73.2 |

Assays

General Procedure for cTnI Assay Using Sensibeads Coated with Embodiments of the Present Copolymers:

All assays were performed on a DIMENSION® VISTA® instrument (Siemens Healthcare Diagnostics Inc., Newark Del.) (Siemens). Briefly, cover on well #8 of a commercial cTnI flex cartridge (Siemens Healthcare Diagnostics catalog #K6421) was punctured. The commercial cTnI product utilizes LOCI technology and reagents. Dextran-coated sensibead suspension of the commercial product was aspirated out and the copolymer-coated sensibead suspension (0.7 mL, 1.5 mg sensibead/mL BSA wash buffer) was added to the cleaned well. The cTnI assay was then run using calibrators as samples according to the manufacturer's instructions supplied with the product. No optimization was carried out either for instrument parameters, buffer formulations, or concentration of reagents employed. Results of assays are summarized below in Table 3 (SB 1), Table 4 (SB 2), Table 5 (SB 3), Table 6 (SB 4), Table 7 (SB 5), Table 8 (SB 6), Table 9 (SB 7) and Table 10 (SB 8).

TABLE 3

Assays using SB 1
LOCI Signal (kcounts)

| Calibrator | ng/mL | Rep 1 | Rep 2 | Rep 3 | Mean | SD | % CV |
|---|---|---|---|---|---|---|---|
| L1 | 0.00 | 6.67 | 6.69 | 6.61 | 6.66 | 0.04 | 0.6% |
| L2 | 0.48 | 19.96 | 20.15 | 19.68 | 19.93 | 0.24 | 1.2% |
| L3 | 4.30 | 185.09 | 182.21 | 182.22 | 183.17 | 1.66 | 0.9% |
| L4 | 8.40 | 418.64 | 421.13 | 423.99 | 421.25 | 2.68 | 0.6% |
| L5 | 20.70 | 1339.86 | 1313.21 | 1334.42 | 1329.16 | 14.08 | 1.1% |
| L6 | 42.90 | 2848.55 | 2825.92 | 2854.27 | 2842.91 | 14.99 | 0.5% |

TABLE 4

Assays using SB 2
LOCI Signal (kcounts)

| Cali-brator | ng/mL | Rep 1 | Rep 2 | Rep 3 | Mean | SD | % CV |
|---|---|---|---|---|---|---|---|
| L1 | 0.00 | 3.46 | 3.46 | 3.31 | 3.41 | 0.09 | 2.5% |
| L2 | 0.48 | 16.18 | 16.17 | 16.14 | 16.16 | 0.02 | 0.1% |
| L3 | 4.30 | 168.59 | 168.17 | 168.73 | 168.50 | 0.29 | 0.2% |
| L4 | 8.40 | 381.76 | 383.77 | 387.01 | 384.18 | 2.65 | 0.7% |
| L5 | 20.70 | 1191.47 | 1188.01 | 1193.07 | 1190.85 | 2.59 | 0.2% |
| L6 | 42.90 | 2580.13 | 2556.88 | 2557.88 | 2564.96 | 13.14 | 0.5% |

TABLE 5

Assays using SB 3
LOCI Signal (kcounts)

| Cali-brator | ng/mL | Rep 1 | Rep 2 | Rep 3 | Mean | SD | % CV |
|---|---|---|---|---|---|---|---|
| L1 | 0.00 | 20.6 | 20.47 | 20.24 | 20.44 | 0.18 | 0.9% |
| L2 | 0.48 | 57.25 | 61.08 | 55.35 | 57.89 | 2.92 | 5.0% |
| L3 | 4.30 | 427.97 | 417.57 | 419.15 | 421.56 | 5.60 | 1.3% |
| L4 | 8.40 | 875.66 | 870.74 | 879.83 | 875.41 | 4.55 | 0.5% |
| L5 | 20.70 | 2153.91 | 2157.21 | 2162.87 | 2158.00 | 4.53 | 0.2% |
| L6 | 42.90 | 3655.09 | 3603.63 | 3639.14 | 3632.62 | 26.34 | 0.7% |

TABLE 6

Assays using SB 4
LOCI Signal (kcounts)

| Cali-brator | ng/mL | Rep 1 | Rep 2 | Rep 3 | Mean | SD | % CV |
|---|---|---|---|---|---|---|---|
| L1 | 0.00 | 3.5 | 3.12 | 3.09 | 3.24 | 0.23 | 7.1% |
| L2 | 0.48 | 8.87 | 8.72 | 9.02 | 8.87 | 0.15 | 1.7% |
| L3 | 4.30 | 74.68 | 73.61 | 73.33 | 73.87 | 0.71 | 1.0% |
| L4 | 8.40 | 167.6 | 170.81 | 167.73 | 168.71 | 1.82 | 1.1% |
| L5 | 20.70 | 538.68 | 533.22 | 538.89 | 536.93 | 3.21 | 0.6% |
| L6 | 42.90 | 1254.19 | 1241.71 | 1232.78 | 1242.89 | 10.75 | 0.9% |

TABLE 7

Assays using SB 5
LOCI Signal (kcounts)

| Cali-brator | ng/mL | Rep 1 | Rep 2 | Rep 3 | Mean | SD | % CV |
|---|---|---|---|---|---|---|---|
| L1 | 0.00 | 5.96 | 5.98 | 5.7 | 5.88 | 0.16 | 2.7% |
| L2 | 0.48 | 6.2 | 6.35 | 6.2 | 6.25 | 0.09 | 1.4% |
| L3 | 4.30 | 12.79 | 12.52 | 12.42 | 12.58 | 0.19 | 1.5% |
| L4 | 8.40 | 20.32 | 20.72 | 20.52 | 20.52 | 0.20 | 1.0% |
| L5 | 20.70 | 52.09 | 52.97 | 52.27 | 52.44 | 0.46 | 0.9% |
| L6 | 42.90 | 121.84 | 121.2 | 121.73 | 121.59 | 0.34 | 0.3% |

TABLE 8

Assays using SB 6
LOCI Signal (kcounts)

| Cali-brator | ng/mL | Rep 1 | Rep 2 | Rep 3 | Mean | SD | % CV |
|---|---|---|---|---|---|---|---|
| L1 | 0.00 | 19.59 | 19.79 | 18.24 | 19.21 | 0.84 | 4.4% |
| L2 | 0.48 | 26.82 | 24.69 | 26.71 | 26.07 | 1.20 | 4.6% |
| L3 | 4.30 | 81.16 | 83.34 | 79.84 | 81.45 | 1.77 | 2.2% |
| L4 | 8.40 | 153.17 | 142.64 | 144.11 | 146.64 | 5.70 | 3.9% |
| L5 | 20.70 | 367.98 | 370.68 | 329.42 | 356.03 | 23.08 | 6.5% |
| L6 | 42.90 | 685 | 625.57 | 677.17 | 662.58 | 32.29 | 4.9% |

TABLE 9

Assays using SB 7
LOCI Signal (kcounts)

| Cali-brator | ng/mL | Rep 1 | Rep 2 | Rep 3 | Mean | SD | % CV |
|---|---|---|---|---|---|---|---|
| L1 | 0.00 | 4.25 | 4.29 | 4.72 | 4.42 | 0.26 | 5.9% |
| L2 | 0.48 | 5.37 | 5.73 | 5.51 | 5.54 | 0.18 | 3.3% |
| L3 | 4.30 | 19.8 | 19.47 | 19.91 | 19.73 | 0.23 | 1.2% |
| L4 | 8.40 | 40.74 | 40.55 | 41.37 | 40.89 | 0.43 | 1.0% |
| L5 | 20.70 | 126.38 | 125.28 | 123.42 | 125.03 | 1.50 | 1.2% |
| L6 | 42.90 | 317.63 | 316.73 | 319.54 | 317.97 | 1.43 | 0.5% |

TABLE 10

Assays using SB 8
LOCI Signal (kcounts)

| Cali-brator | ng/mL | Rep 1 | Rep 2 | Rep 3 | Mean | SD | % CV |
|---|---|---|---|---|---|---|---|
| L1 | 0.00 | 3.55 | 3.45 | 3.8 | 3.60 | 0.18 | 5.0% |
| L2 | 0.48 | 9.06 | 9.07 | 8.61 | 8.91 | 0.26 | 2.9% |
| L3 | 4.30 | 66.07 | 65.5 | 66.3 | 65.96 | 0.41 | 0.6% |
| L4 | 8.40 | 144.2 | 146 | 145.83 | 145.34 | 0.99 | 0.7% |
| L5 | 20.70 | 386.51 | 390.04 | 383.37 | 386.64 | 3.34 | 0.9% |
| L6 | 42.90 | 727.9 | 740.82 | 730 | 732.91 | 6.93 | 0.9% |

General Procedure for cTnI Assay using SB 2 and CB 2:

All assays were performed on a DIMENSION® VISTA® instrument (Siemens Healthcare Diagnostics Inc., Newark Del.) (Siemens). Briefly, cover on well #8 of a commercial cTnI flex cartridge was punctured. Dextran-coated sensibead suspension was aspirated out and SB 2 suspension (0.7 mL, 1.5 mg SB 2/mL BSA wash buffer) was added into the cleaned well. In addition, chemibeads of the commercial cTnI product were replaced with CB 2 (0.9 mL, 0.19 mg CB 2/mL BSA wash buffer). The cTnI assay was then run using calibrators as samples according to the manufacturer's instructions supplied with the product. No optimization was carried out either for instrument parameters, buffer formulations, or concentration of reagents employed. Results of assays are summarized below in Table 11.

TABLE 11

Assays using SB 2 and CB 2
LOCI Signal (kcounts)

| Cali-brator | ng/mL | Rep 1 | Rep 2 | Rep 3 | Mean | SD | % CV |
|---|---|---|---|---|---|---|---|
| L1 | 0.00 | 15.84 | 15.86 | 16.11 | 15.94 | 0.15 | 0.9% |
| L2 | 0.48 | 17.8 | 17.3 | 17.91 | 17.67 | 0.33 | 1.8% |
| L3 | 4.30 | 39.62 | 40.2 | 39.35 | 39.72 | 0.43 | 1.1% |
| L4 | 8.40 | 70.01 | 68.5 | 66.93 | 68.48 | 1.54 | 2.2% |
| L5 | 20.70 | 176.42 | 177.26 | 178.42 | 177.37 | 1.00 | 0.6% |
| L6 | 42.90 | 370.14 | 379.3 | 381.45 | 376.96 | 6.01 | 1.6% |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A composition for use as an assay reagent, the composition comprising:
   a solid support comprising a member of a signal producing system and a coating of a synthetic copolymer wherein the synthetic consists of
   (i) a first copolymerized monomer comprising a pendant moiety wherein the pendant moiety has the formula:

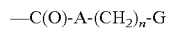
   —C(O)-A-(CH$_2$)$_n$-G wherein A is NR$^1$ wherein R$^1$ is H or alkyl of from 1 to 6 carbon atoms and n is 1 to 10 and wherein G is CHO; CH(OR$^8$)$_2$ wherein R$^8$ is alkyl of from 1 to 6 carbon atoms; or a member of a specific binding pair; and
   (ii) a second copolymerized monomer comprising a pendant moiety wherein the pendant moiety has the formula:

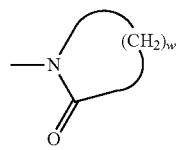

wherein:
   w is 2-4.

2. The composition according to claim 1 wherein the solid support is a particle.

3. The composition according to claim 2 wherein the particle is a latex particle.

4. The composition according to claim 1 wherein the member of the signal producing system is selected from the group consisting of sensitizers and chemiluminescent compounds.

5. The composition according to claim 1 wherein the copolymer comprises an polyethylenic backbone.

6. The composition according to claim 1 wherein the pendant moiety of the first copolymerized monomer is —C(O)—NH—(CH$_2$)$_n$—CHO or —C(O)—NH—(CH$_2$)$_n$—CH(OCH$_3$)$_2$ wherein n is 1.

7. The composition according to claim 1 wherein the pendant moiety of the second copolymerized monomer is

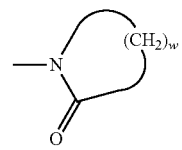

wherein:
   w is 3.

8. The composition according to claim 1 wherein a member of a specific binding pair is associated with the solid support.

9. A method of determining in a sample the presence and/or amount of an analyte, the method comprising:
   (a) providing in combination in a medium:
      (i) the sample, and
      (ii) the composition according to claim 8 wherein the member of the specific binding pair (sbp) binds to the analyte or to a second sbp member to form a complex related to the presence of the analyte,
   (b) subjecting the combination to conditions for binding of the analyte to the composition to form a complex, and
   (c) activating the member of the signal producing system and detecting the amount of the complex, the amount of the complex being related to the presence and/or amount of analyte in the sample.

10. A method of determining in a sample the presence and/or amount of an analyte, the method comprising:
   (a) providing in combination in a medium:
      (i) the sample, and
      (ii) a composition comprising:
      a particle comprising:
         (A) a member of a signal producing system,
         (B) a member of the specific binding pair that binds to the analyte or to a second sbp member to form a complex related to the presence of the analyte and
         (C) a coating of a copolymer of the formula:

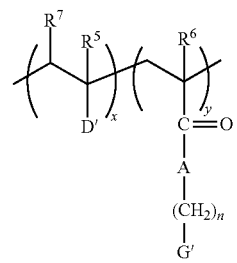

wherein:
   A is NR$^1$ wherein R$^1$ is H or alkyl of from 1 to 6 carbon atoms;
   n is 1 to 10;

G is CHO; CH(OR$^8$)$_2$ wherein R$^8$ is alkyl of from 1 to 6 carbon atoms or a member of a specific binding pair;

D is

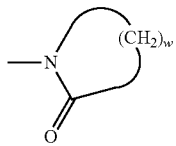

wherein:

w is 2-4;

(b) subjecting the combination to conditions for binding of the member of the specific binding pair to the analyte or to the second specific binding pair member to form a complex; and (c) activating the member of the signal producing system and detecting the amount of the complex, the amount of the complex being related to the presence and/or amount of analyte in the sample.

11. The method according to claim 10 wherein the member of the signal producing system is selected from the group consisting of sensitizers and chemiluminescent compounds.

12. The method according to claim 10 wherein the member of the signal producing system is incorporated into the particle.

13. The method according to claim 10 wherein the member of the signal producing system is a photosensitizer and the combination further comprises a chemiluminescent reagent or wherein the member of the signal producing system is a chemiluminescent compound and the combination further comprises a photosensitizer reagent.

* * * * *

UNITED STATES PATENT AND TRADEMARK OFFICE
CERTIFICATE OF CORRECTION

| | | |
|---|---|---|
| PATENT NO. | : 8,546,148 B2 | Page 1 of 1 |
| APPLICATION NO. | : 13/442503 | |
| DATED | : October 1, 2013 | |
| INVENTOR(S) | : Bhalchandra Lele et al. | |

It is certified that error appears in the above-identified patent and that said Letters Patent is hereby corrected as shown below:

In the Claims:

In Claim 1, Column 37, line 32, after "the synthetic" please insert --copolymer--.

Signed and Sealed this
Twenty-second Day of July, 2014

Michelle K. Lee
*Deputy Director of the United States Patent and Trademark Office*